US 7,217,266 B2

(12) United States Patent
Anderson et al.

(10) Patent No.: US 7,217,266 B2
(45) Date of Patent: May 15, 2007

(54) APPARATUS AND METHOD FOR LASER TREATMENT WITH SPECTROSCOPIC FEEDBACK

(76) Inventors: R. Rox Anderson, 399 Marrett Rd., Lexington, MA (US) 02421; Ian W. Hunter, 6 Oakdale La., Lincoln, MA (US) 01773; Colin J. H. Brenan, 19 Jersey St., Marblehead, MA (US) 01945; Keng Hui Lim, 550 Memorial Dr., Apt. 18D-3, Cambridge, MA (US) 02139; Elizabeth Sebern, 9149 Edge O'Woods Dr., Cedarburg, WI (US) 53012

( * ) Notice: Subject to any disclaimer, the term of this patent is extended or adjusted under 35 U.S.C. 154(b) by 428 days.

(21) Appl. No.: 09/870,544

(22) Filed: May 30, 2001

(65) Prior Publication Data
US 2003/0036751 A1 Feb. 20, 2003

(51) Int. Cl.
*A61B 18/18* (2006.01)
*A61B 18/20* (2006.01)

(52) U.S. Cl. .............................. 606/12; 606/9; 606/10; 607/88

(58) Field of Classification Search ................ 606/3–6, 606/8–12; 607/88, 89; 351/208–212; 600/101, 600/104, 108, 118
See application file for complete search history.

(56) References Cited

U.S. PATENT DOCUMENTS

| | | | |
|---|---|---|---|
| 3,865,113 A | 2/1975 | Sharon et al. | |
| 4,266,549 A | 5/1981 | Kimura | |
| 4,517,973 A | 5/1985 | Sunago et al. | |
| 4,785,806 A | 11/1988 | Deckelbaum | |
| 5,071,417 A * | 12/1991 | Sinofsky | 606/8 |
| 5,275,594 A | 1/1994 | Baker et al. | |
| 5,350,376 A * | 9/1994 | Brown | 606/12 |
| 5,366,456 A | 11/1994 | Rink et al. | |
| 5,409,481 A * | 4/1995 | Poppas et al. | 606/12 |
| 5,501,680 A | 3/1996 | Kurtz et al. | |
| 5,507,287 A | 4/1996 | Palcic et al. | |
| 5,634,920 A | 6/1997 | Hohla | |
| 5,653,706 A | 8/1997 | Zavislan et al. | |
| 5,662,643 A * | 9/1997 | Kung et al. | 606/3 |
| 5,741,215 A | 4/1998 | D'Urso | |

(Continued)

FOREIGN PATENT DOCUMENTS

WO        WO 00/62700        10/2000

OTHER PUBLICATIONS

Sebern et al. "Laser treatment of nevus flammus (portwine stain) with spectroscopic feedback: the smart scalpel," Proc. SPIE, vol. 3519, pp. 32-42, 1999.*

(Continued)

*Primary Examiner*—A. Farah
(74) *Attorney, Agent, or Firm*—Edwards Angell Palmer & Dodge LLP

(57) ABSTRACT

A platform Smart Scalpel system using rapid real-time feedback for effecting laser treatment. The platform system includes an imaging system for rapid real-time detection of tissue characteristics, a processing system for processing the detected characteristics, and a treatment system for effecting treatment in accordance with results of the processing. The platform system provides for preprogramming and real-time inputting conditions and parameters for diagnosis using the imaging system and/or treatment using the treatment system.

37 Claims, 29 Drawing Sheets

U.S. PATENT DOCUMENTS

| | | | |
|---|---|---|---|
| 5,813,403 A | 9/1998 | Soller et al. | |
| 5,827,264 A | 10/1998 | Hohla | |
| 5,860,967 A * | 1/1999 | Zavislan et al. | 606/9 |
| 5,865,828 A | 2/1999 | Jeng | |
| 5,865,832 A | 2/1999 | Knopp et al. | |
| 5,931,779 A | 8/1999 | Arakaki et al. | |
| 5,943,354 A | 8/1999 | Lawandy | |
| 5,963,676 A | 10/1999 | Wu et al. | |
| 5,984,915 A | 11/1999 | Loeb et al. | |
| 6,006,119 A | 12/1999 | Soller et al. | |
| 6,015,404 A * | 1/2000 | Altshuler et al. | 606/9 |
| 6,047,080 A | 4/2000 | Chen et al. | |
| 6,146,390 A | 11/2000 | Heilbrun et al. | |
| 6,159,202 A | 12/2000 | Sumiya et al. | |
| 6,190,377 B1 | 2/2001 | Kudrall | |
| 6,210,401 B1 * | 4/2001 | Lai | 606/12 |
| 6,315,773 B1 * | 11/2001 | Frey et al. | 606/12 |
| 6,436,127 B1 * | 8/2002 | Anderson et al. | 607/89 |
| 6,610,051 B2 * | 8/2003 | Bille | 606/5 |
| 6,984,228 B2 * | 1/2006 | Anderson et al. | 606/9 |

OTHER PUBLICATIONS

Bantel et al., Global Tracking of the Ocular Fundus Pattern Imaged by Scanning Laser Ophthalmoscopy, International Journal Biomedical Computing, vol. 27, 1990, pp. 59-69.

E.L. Sebem, C.J.H. Brènan, R.R. Anderson, and I.W. Hunter, Laser treatment of nevus flammus (port wine stain) with spectroscopic feedback: 'The Smart Scalpel' *Proc. SPIE*, vol. 3519, pp. 32-42, 1999.

E.L. Sebem, C.J.H. Brenan, R.R. Anderson, and I.W. Hunter, Tissue modification with feedback: the 'Smart Scalpel'*Proc. SPIE*, vol. 3519, pp. 62-69, 1998.

J.H.C. Inderfurth, R.D. Ferguson, M.B. Frish, and R. Birngruber, Dynamic reflectometer for control of laser photocoagulation on the retina *Lasers in Surgery and Medicine*, vol. pp. 54-61, 1994.

E. L. Sebem, C.J.H. Brenan, R.R. Anderson and I.W. Hunter, Design and Characterization of a laser-based instrument with spectroscopic feedback control for treatment of vascular lesions: the Smart Scalpel, Journal of Biomedical Optics, Oct. 2000, vol. 05(04), pp. 375-382.

R.B. Stewart, A. Brenbrahim, G.M. LaMuraglia, M. Rosenberg, G.J. L'Italien, W.M. Abbott, and R.T.V. Kung, Laser assisted vascular welding with real time temperature control Lasers in Surgery and Medicine, vol. pp. 9-16, 1996.

Pfefer, TJ. et al., *Modeling Laser Treatment of Port Wine Stains With a Computer-Reconstructed Biopsy*, Lasers in Surgery and Medicine, vol. 24, Sep. 1998 (Published 1999), pp. 151-166.

Verkruysse, W. et al. *Simulation of Color of Port Wine Stain Skin and Its Dependence on Skin Variables*, Lasers in Surgery and Medicine, vol. 25, Mar. 1999 (Published 1999), pp. 131-139.

Wimmershoff, M.B. et al., *Mixed Capillary/Lymphatic Malformation with Coexisting Port-Wine Stain: Treatment Utilizing 3D MRI and CT-Guided Sclerotherapy*, Dermatologic Surgery, vol. 26, No. 6, Jun. 2000, pp. 584-587.

Verkruysse, W. et al., *Optical Absorption of Blood Depends on Temperature during a 0.5 ms Laser Pulse at 586 nm*, Photochemistry and Photobiology, vol. 67, No. 3, Dec. 1997 (Published 1998), pp. 276-281.

Welch A.J. et al., *Monte Carlo Model for Determination of the Role of Heat Generation in Laser-Irradiated Tissue*, Journal of Biomechanical Engineering, vol. 119, Nov. 1997, pp. 489-495.

Garrand T.J. et al., *Design and Evaluation of a Fiberoptic Fluorescence Guided Laser Recanalization System*, Lasers in Surgery and Medicine, vol. 11, Oct. 1990 (Published 1991), pp. 106-116.

O'Brien, K.M. et al., *Development and Evaluation of Spectral Classification Algorithms for Fluorescence Guided Laser Angioplasty*, IEEE Transactions on Biomedical Engineering, vol. 36, No. 4, Apr. 1989, pp. 424-430.

L. Reinisch, M.H. Mendenhall, and R.H. Ossoff, Precise laser incisions, corrected for patient respiration with an intelligent aiming system *Lasers in Surgery and Medicine*, vol. pp. 210-215, 1997.

Sandia National Laboratories, Cancer cells detected in seconds by 'smart scalpel' device. Url: www.sandia.gov/Solution.htm#Bio. 2000.

R. Rox Anderson, Laser medicine in dermatology *The Journal of Dermatology*, vol. 23, pp. 778-782, 1996.

Serge Mordon, Guy Rotteleur, Jean Marc Brunetaud, and David B. Apfelberg, Rationale for automatic scanners in laser treatment of port wine stains *Lasers in Surgery and Medicine*, vol. pp. 113-123, 1993.

RJ. Elble, Physiologic and essential tremor *Neurology*, vol. pp. 225-231, 1986.

American Academy of Family Physicians, Classification of tremor and update on treatment, Url: www.aafp.org/afp/990315ap/1565.html.

S.H. Barsky, S. Rosen, D.E. Geer, and J.M. Noe, The nature and evolution of port wine stains: a computer-assisted study *The Journal of Investigative Dermatology*, vol. pp. 154-157, 1980.

M.J.C. van Gemert, J.S. Nelson, T.E. Milner, D.J. Smithies, W. Verkruysse, J.F. de Boer, G.W. Lucassen, D.M. Goodman, B.S. Tanenbaum, and L.T. Norvang, L. O. S., Non-invasive determination of port wine stain anatomy and physiology for optimal laser treatment strategies *Physics in Medicine and Biology*, vol. pp. 937-950, 1997.

O.T. Tan, P. Morrison, and A.K. Kurban, 585 nm for the treatment of portwine stains *Plastic Reconstruction Surgery*, vol. pp. 1112-1117, 1990.

A.L. McKenzie, Physics of thermal processes in laser-tissue interactions *Phys. Med Biol.*, vol 35, pp. 1175-1209, 1990.

C.C. Dierickx, J. M. Casparian, V. Venugopalan, W.A. Farinelli, and R.R. Anderson, Thermal relaxation of port wine stain vessels probed in vivo: the need for 1-10 millisecond laser pulse treatment *The Journal of Investigative Dermatology*, vol. 105, pp. 709-714, 1995.

W.F. Cheong, S.A. Prahl, and A.J. Welch, A Review of the Optical Properties of Biological Tissues *IEEE Journal of Quantum Electronics*, vol. 26, pp. 2166-2185, 1990.

M. J. C. Van Gemert , J. W. Pickering, A. J. Welch, and O. T. Tan, Modeling laser treatment of port wine stains *Management and treatment of benign cutaneous vascular lesions*, vol. pp. 24-47, 1992.

W. Verkuysse, J. W. Pickering, J. Beek, M. Keijzer, and M. J. C. van Gemert, Modelling the effect of wavelength on the pulsed dye laser treatment of port wine stains *Applied Optics*, vol. pp. 393-398, 1993.

R. Rox Anderson, Polarized light examination and photography of the skin *Archives of Dermatology*, vol. 127(7), pp. 1000-1005, 1991.

J.B. Dawson, D.J. Barker, D.J. Ellis, E. Grassam, J.A. Cotterill, G.W. Fisher, and J.W. Feather, A theoretical and experimental study of light absorption and scattering by in vivo skin *Physics in Medicine and Biology*, vol. 25, pp. 695-709, 1980.

K.P. Watts, R.G. Fairchild, D.N. Slatkin, D. Greenberg, S.Packer, H.L. Atkins, and S.J. Hannon, Melanin content of hamster tissues, human tissues, and various melanomas *Cancer Research*, vol. pp. 467-472, 1981.

R. Rox Anderson and John A. Parrish, The Optics of Human Skin *The Journal of Investigative Dermatology*, vol. 77, pp. 13-19, 1981.

B.C. Wilson and S.L. Jacques, Optical reflectance and transmittance of tissues: principles and applications *IEEE Journal of Quantum Electronics*, vol. 26, pp. 2186-2199, 1990.

B.G. Schunck, Edge Detection with Gaussian Filters at Multiple Scales of Resolution *Advances in Image Analysis*, vol. pp. 75-105, 1992.

F. Holler, D. Burns, and J. Callis, "Direct use of second derivatives in curve-fitting procedures." Applied Spectroscopy, vol. 43, No. 5 (1989) 877-882.

M. Blanco, A. Eustaquio, J.M. Gonzalez, D. Serrano, "Identification and quantification assays for intact tablets of two related pharmaceutical preparations by reflectance near-infrared spectroscopy: validation of the procedure", Journal of Pharmaceutical and Biomedical Analysis, 22 (2000) 139-148.

J.M. Schmitt, A. Knuttel, and R.F. Booner, Measurement of optical properties of biological tissues by low-coherence reflectometry *Applied Optics*, vol. 32, pp. 6032-6042, 1993.

R.T. Strebel, U. Utzinger, M. Peitola, J. Schneider, P.F. Niederer, and O.M. Hess, "Excimer laser spectroscopy: Influence of tissue ablation on vessel wall fluorescence." Journal of Laser Applications, vol. 10, No. 1 Feb. 1998, 34-40.

Morguet, A.J. et al., *Design and Evaluation of a Spectroscopy System to Classify Laser-induced Arterial Fluorescence Spectra*, Biomedizinische Technik, vol. 42, No. 6, 1997, pp. 176-182 (in German; English abstract).

T. Lindeberg, Discrete derivative approximations with scale-space properties: A basis for low-level feature extraction *Journal of Mathematical Imaging and Vision*, vol. 3, pp. 349-376, 1993.

D. Eberly, R. Gardner, B. Morse, S. Pizer, and C. Scharlach, Ridges for image analysis *Journal of Mathematical Imaging and Vision*, vol. 4, pp. 351-371, 1994.

F.C. Glazer, Fiber identification in microscopy by ridge detection and grouping *Proceedings of the IEEE Workshop on Applications of Computer Vision*, vol. pp. 205-212, 1992.

C. Steger, Extracting Curvilinear Structures: A Differential Geometric Approach *Fourth European Conference on Computer Vision, Lecture Notes in Computer Science*, vol. 1064, pp. 630-641, 1996.

O. Monga, N. Armande, and P. Montesinos, Thin nets and crest lines: application to satellite data and medical images *Computer Vision and Image Understanding*, vol. 67, pp. 285-295, 1997.

J. Canny, A Computational Approach to Edge Detection *IEEE Transaction on Pattern Analysis and Machine Intelligence*, vol. PAMI 8, pp. 679-698, 1986.

R.S. Afzal, A.W. Yu, J.J. Zayhowski, and T.Y. Fan, Single Mode, High Peak Power, Passively Q-Switched Diode-Pumped Nd:YAG Laser *Optics Letters*, vol. 22, pp. 1314-1316, 1997.

C.D. Nabors, J.J. Zayhowski, R.L. Aggarwal, J.R. Ochoa, J.L. Daneu, and A. Mooradian, High-Power Nd:YAG Microchip Laser Arrays *Optical Society of America Proceedings on Advanced Solid-State Lasers*, vol. 13, pp. xxvii+391, 234-236, 1992.

J.J. Zayhowski, Microchip Lasers Create Light in Small Places *Laser Focus World*, vol. 32, pp. 73-74 & 76-78, 1996.

Arakawa, K. et al., *XeCl Excimer Laser-Induced Fluorescence for Selective Ablation of Atheromatous Tissue*, Japanese Circulation Journal, vol. 55, Nov. 1991, pp. 1094-1105.

J.P. Fischer, J. Dams, M.H. Gotz, E. Kerker, F.H. Loesel, C.J. Messer, M.H. Niemz, N. Suhm and J.F. Bille, Plasma-Mediated Ablation of Brain Tissue with Picosecond Laser Pulses, *Applied Physics B*. 58: 493-499 (1994).

E.J. Fiskerstrand, L.O. Svaasand, G. Kopstad, M. Dalaker, L.T. Norvang and G. Volden, Laser Treatment of Port Wine Stains: Therapeutic Outcome in Relation to Morphological Parameters, *British Journal of Dermatology*, 136(3): 467-8 (1997).

S.L. Jacques, C.A. Alter and S.A. Prahl, Angular Dependence of HeNe Laser Light Scattering by Human Dermis, *Laser Life Sci.* 1: 309-333 (1987).

L.O. Reynolds, C.C. Johnson and A. Ishimaru, Diffuse Reflectance from a Finite Blood Medium: Applications to the Modeling of Fiber Optic Catheters. *Appl. Opt.*, 15: 2059-2067 (1976).

Richards-Kortum, R. et al., *476 nm Excited laser-induced fluorescence spectroscopy of human coronary arteries: Applications in cardiology*, American Heart Journal, vol. 122, Oct. 1991, pp. 1141-1150.

A. Solan, V. Prabhakar, and L. Niklason, "Engineered Vessels: Importance of the Extracellular Matrix", Transplantation Proceedings, 33, 66-68 (2001).

L. Deckelbaum, M.D., D. Sameer, K. Chang, and J. Scott. "Evaluation of a Fluorescence Feedback System for Guidance of Laser Angioplasty." Lasers in Surgery and Medicine 16: 226-234 (1995).

Andersson-Engels, S. et al., *Time-Resolved Laser-Induced Fluorescence Spectroscopy for Enhanced Demarcation of Human Atherosclerotic Plaques*, Journal of Photochemistry and Photobiology, vol. 4, Part. B, 1990, pp. 363-369.

* cited by examiner

| Laser | Wavelength (nm) | Treat Fluence (J/cm$^2$) | Type |
|---|---|---|---|
| Argon | 488, 514 | 1-10 | CW |
| Classic KTP | 532 | 10-40 | CW |
| Cu or Cu-Br | 512-578 | 1-10 | CW |
| Krypton | 570 | 1-10 | CW |
| Pulse dye (yellow) | 585 | 4-8 | Pulsed |
| Derm-KTP | 532 | 2-20 | Pulsed |
| Pulsed dye (green) | 510 | 3-5 | Pulsed |
| Q-sw. Nd:YAG – green<br>              - infrared | 532<br>1064 | 3-5<br>4-10 | Pulsed |
| Q-sw. Ruby (red) | 694 | 4-10 | Pulsed |
| Q-sw. Alexandrite (infrared) | 755 | 4-10 | Pulsed |

FIG. 5

| Tissue | λ (nm) | $\mu_a$ (mm$^{-1}$) | $\mu_s$ (mm$^{-1}$) | G | $\mu_s'$ (mm$^{-1}$) | $\mu_t$ (mm$^{-1}$) |
|---|---|---|---|---|---|---|
| Human dermis | 633 | 0.27 | 18.7 | 0.81 | 3.553 | 3.823 |

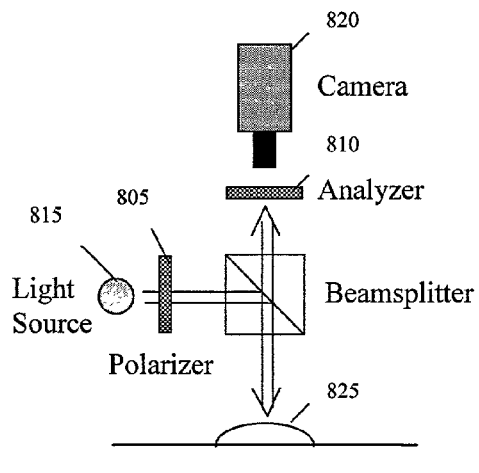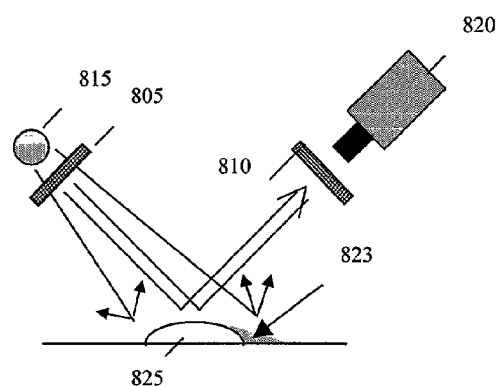
FIG. 8A  FIG. 8B
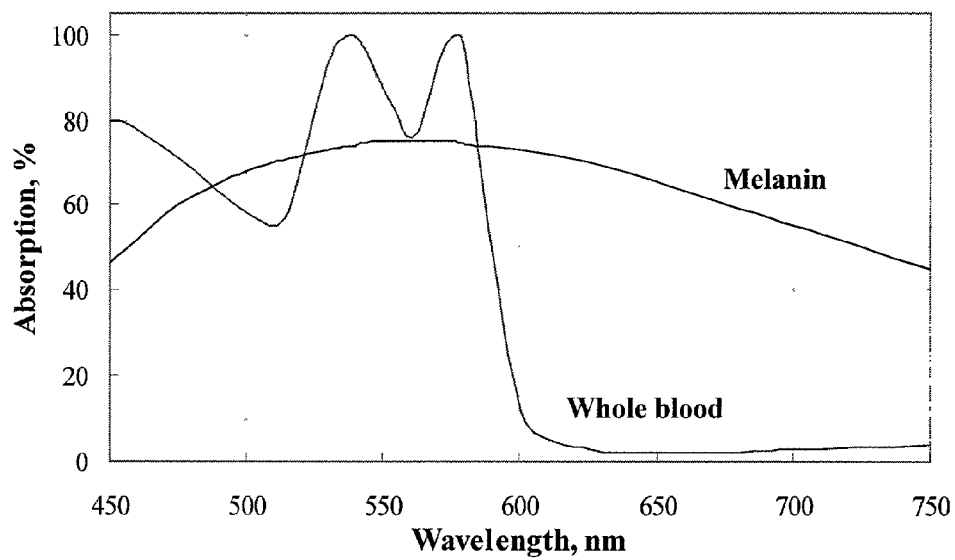
FIG. 9

Parabolic Line Profile

First Derivative Profile

Second Derivative Profile

 
FIG. 20A   FIG. 20B
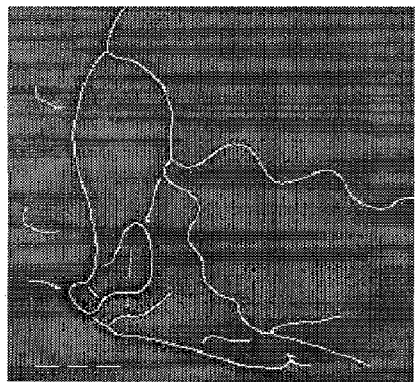
FIG. 20C

| No. | Process | Time (sec) |
|---|---|---|
| 1. | Direct Convolution: $\sigma = 3.0$ | 3.9 |
| 2a. | Recursive Filtering: $\sigma = 3.0$<br>$4^{th}$ order IIR filter | 3.3 |
| 2b. | $3^{rd}$ order IIR filter | 3.0 |

FIG. 23

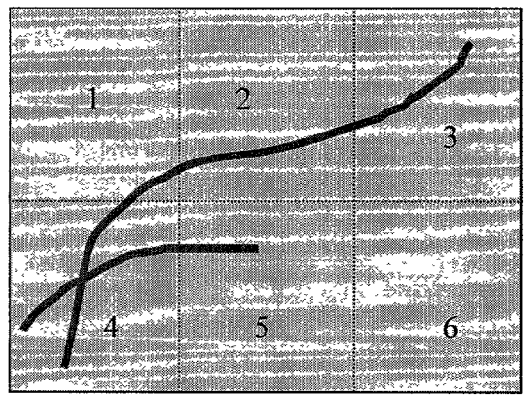
FIG. 24A
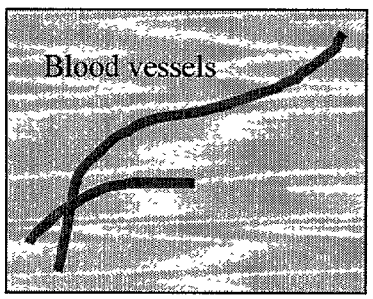  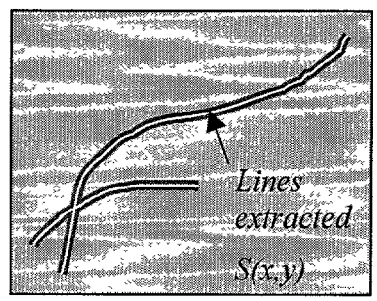
FIG. 24B          FIG. 24C

| Laser | Coherent Innova 100 CW Argon Laser |
|---|---|
| Wavelength | 514 nm |
| Beam diameter | 750 μm |
| Power | 1 watt |
| Pulse width | 80 ms (CW laser pulsed mechanically) |
| Fluence | $18.1 \times 10^4$ J/m$^2$ |

*Treatment laser parameters*

FIG. 28

Blood vessels before treatment (illumination at 577 nm).

Targets identified by the Smart Scalpel.

Blood vessels immediately after treatment.

*Histology results*

*Close-up view showing coagulated blood vessels*

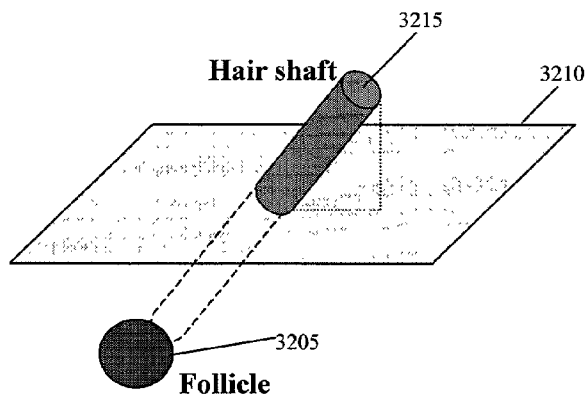
FIG. 32A
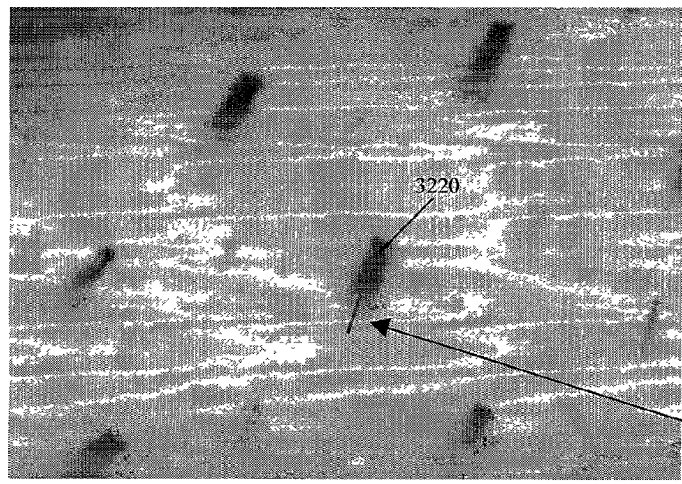
FIG. 32B
Hair follicle beneath the skin can lie anywhere along this red line.
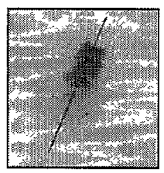 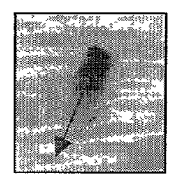
FIG. 32C     FIG. 32D

APPARATUS AND METHOD FOR LASER TREATMENT WITH SPECTROSCOPIC FEEDBACK

FIELD OF THE INVENTION

The present invention relates to a laser treatment apparatus and method that utilizes continuous feedback control for locating and identifying treatment targets and for delivering appropriate treatment to the treatment targets.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference.

BACKGROUND OF THE INVENTION

Medical procedures where laser light is directed at tissue for treatment have been in use. Most of the laser treatment methods used today share a common disadvantage: all require great expertise with poor reproducibility, and this creates a great variation in the results. There are reported problems such as hypertrophic scarring and inhomogeneity of blanching due to inhomogeneous energy delivery and dosage. In addition, these manual methods are tedious and time-consuming, and usually require several sessions over a period of months.

Furthermore, many conventional methods require manually moving a handpiece over a treatment area, and as a result, this movement is operator dependent and duplication of initial treatment motion is not possible with subsequent applications. Movement of the beam out of focus and variation in the angle of the beam modify the spot size. The speed of the handpiece moving across the lesion is also not controlled. Therefore, each of these inconsistencies may result in very inaccurate coverage due to poor dosimetry.

As a result, laser tools that incorporate additional features for aiding the operator of such laser tools in providing effective treatment have been in development.

With respect to laser treatment apparatuses with various target location and control schemes, reference is made to the following:

Kurtz et al., U.S. Pat. No. 5,501,680, relates to a laser operation and control system comprising a laser, control circuitry for activating and deactivating the laser, a boundary sensor, and a proximity sensor.

Hohla, U.S. Pat. No. 5,634,920, and Hohla, U.S. Pat. No. 5,827,264, each discloses a technique for controlling a laser apparatus for removing tissue from the eye that uses oscillating, or dithering, to prevent reinforcing ridges from being formed during the tissue removal process.

Jeng, U.S. Pat. No. 5,865,828, is directed to a coaxial dual laser apparatus for ablating surface lesions gated by the degree of surface small vessel blood flow via detection of Doppler shift.

Knopp et al., U.S. Pat. No. 5,865,832, discloses the use of pattern recognition and edge detection methods in correlation trackers for tracking the human cornea for laser treatment.

Arakaki et al., U.S. Pat. No. 5,931,779, involves a technique for measuring the absorption spectrum of tissue using spectrographic equipment for non-invasively taking spectroscopic measurements of tissue. The measured spectrum is corrected for light scattering effects, such as by taking the second derivative of the data.

Chen et al., U.S. Pat. No. 6,047,080, relates to a method for in-room computer reconstruction of a three-dimensional (3-D) coronary arterial tree from routine biplane angiograms acquired at arbitrary angles and without using calibration objects. The method includes, among other steps, detecting, segmenting and identifying vessel centerlines and constructing a vessel hierarchy representation.

Wu et al., U.S. Pat. No. 5,963,676, involves a method of enhancing an image in X-ray angiography that includes preprocessing an input image using an edge-preserving smoothing filter to reduce noise effect.

Heilbrun et al., U.S. Pat. No. 6,146,390, is directed to a technique for defining the location of a medical instrument relative to features of a medical workspace including a patient's body region. Image filtering and edge detection are used for defining the edges of an instrument.

Kudrall, U.S. Pat. No. 6,190,377, relates to a technique for predicting an effective and safe laser light energy range for sub-epidermal laser surgery. The method includes first impinging a measurement laser pulse on a predetermined treatment area. The thermal emission caused by the measurement laser pulse emanating from the treatment area is then detected and the delay time from the measurement laser pulse to the detection of the thermal emission is measured. The rise rate of the thermal emission is then measured. The layer thickness is then calculated based upon the delay time, wherein the layer thickness is substantially the epidermal thickness. An internal measurement temperature rise is calculated based upon the layer thickness and the rise rate.

Bantel et al., *Global Tracking of the Ocular Fundus Pattern Imaged by Scanning Laser Ophthalmoscopy*, International Journal Biomedical Computing, Vol. 27, 1990, pp. 59–69, discloses using a tracking algorithm that includes edge equalization to process a scanning laser ophthalmoscopic ("SLO") image.

Each of these references provides laser apparatuses with various target location and control features. None of these patents, however, discloses or suggests a laser treatment apparatus with a flexible control platform that provides for accurate, real-time, and non-invasive targeting and treatment for different types of procedures.

It has therefore been found desirable to design a laser treatment apparatus with the advantages as noted below.

The following are hereby incorporated by reference:

E. L. Sebern, C. J. H. Brenan, R. R. Anderson, and I. W. Hunter, Laser treatment of nevus flammus (port wine stain) with spectroscopic feedback: 'The Smart Scalpel' *Proc. SPIE*, vol. 3590, pp. 32–42, 1999;

E. L. Sebern, C. J. H. Brenan, R. R. Anderson, and I. W. Hunter, Tissue modification with feedback: the 'Smart Scalpel' *Proc. SPIE*, vol. 3519, pp. 62–69, 1998.;

E. L. Sebern, Laser treatment of hemangiomas using spectroscopic feedback: The 'Smart Scalpel' *Masters Thesis, MIT Mechanical Engineering Dept*, 1999;

J. H. C. Inderfurth, R. D. Ferguson, M. B. Frish, and R. Birngruber, Dynamic reflectometer for control of laser photocoagulation on the retina *Lasers in Surgery and Medicine*, vol. pp. 54–61, 1994;

R. B. Stewart, A. Benbrahim, G. M. LaMuraglia, M. Rosenberg, G. J. L'Italien, W. M. Abbott, and R. T. V. Kung, Laser assisted vascular welding with real time temperature control *Lasers in Surgery and Medicine*, vol. pp. 9–16, 1996;

L. Reinisch, M. H. Mendenhall, and R. H. Ossoff, Precise laser incisions, corrected for patient respiration with an intelligent aiming system *Lasers in Surgery and Medicine*, vol. pp. 210–215, 1997;

Sandia National Laboratories, Cancer cells detected in seconds by 'smart scalpel' device. Url: www.sandia.gov/Solution.htm#Bio. 2000;

R. Rox Anderson, Laser medicine in dermatology *The Journal of Dermatology*, vol. 23, pp. 778–782, 1996;

Serge Mordon, Guy Rotteleur, Jean Marc Brunetaud, and David B. Apfelberg, Rationale for automatic scanners in laser treatment of port wine stains *Lasers in Surgery and Medicine*, vol. pp. 113–123, 1993;

R. J. Elble and W C. Koller. *Tremor*, The John Hopkins University Press, Baltimore: 1990;

R J. Elble, Physiologic and essential tremor *Neurology*, vol. pp. 225–231, 1986;

American Academy of Family Physicians, Classification of tremor and update on treatment, Url: www.aafp.org/afp/990315ap/1565.html:

S. H. Barsky, S. Rosen, D. E. Geer, and J. M. Noe, The nature and evolution of port wine stains: a computer-assisted study *The Journal of Investigative Dermatology*, vol. pp. 154–157, 1980;

M. J. C. van Gemert, J. S. Nelson, T. E. Milner, D. J. Smithies, W. Verkruysse, J. F. de Boer, G. W. Lucassen, D. M. Goodman, B. S. Tanenbaum, and L. T. Norvang, L. O. S., Non-invasive determination of port wine stain anatomy and physiology for optimal laser treatment strategies *Physics in Medicine and Biology*, vol. pp. 937–950, 1997;

O. T. Tan, P. Morrison, and A. K. Kurban, 585 nm for the treatment of portwine stains *Plastic Reconstruction Surgery*, vol. pp. 1112–1117, 1990;

A. L. McKenzie, Physics of thermal processes in laser-tissue interactions *Phys. Med Biol.*, vol. 35, pp. 1175–1209, 1990;

C. C. Dierickx, J. M. Casparian, V. Venugopalan, W. A. Farinelli, and R. R. Anderson, Thermal relaxation of port wine stain vessels probed in vivo: the need for 1–10 millisecond laser pulse treatment *The Journal of Investigative Dermatology*, vol. 105, pp. 709–714, 1995;

W. F. Cheong, S. A. Prahl, and A. J. Welch, A Review of the Optical Properties of Biological Tissues *IEEE Journal of Quantum Electronics*, vol. 26, pp. 2166–2185, 1990;

M. J. C. Van Gemert, J. W. Pickering, A. J. Welch, and O. T. Tan, Modelling laser treatment of port wine stains *Management and treatment of benign cutaneous vascular lesions*, vol. pp. 24–47, 1992;

W. Verkruysse, J. W. Pickering, J. Beek, M. Keijzer, and M. J. C. van Gemert, Modelling the effect of wavelength on the pulsed dye laser treatment of port wine stains *Applied Optics*, vol. pp. 393–398, 1993;

J. M. Schmitt, A. Knuttel, and R. F. Booner, Measurement of optical properties of biological tissues by low-coherence reflectometry *Applied Optics*, vol. 32, pp. 6032–6042, 1993;

R. Rox Anderson, Polarized light examination and photography of the skin *Archives of Dermatology*, vol. 127(7), pp. 1000–1005, 1991;

J. B. Dawson, D. J. Barker, D. J. Ellis, E. Grassam, J. A. Cotterill, G. W. Fisher, and J. W. Feather, A theoretical and experimental study of light absorption and scattering by in vivo skin *Physics in Medicine and Biology*, vol. 25, pp. 695–709, 1980;

K. P. Watts, R. G. Fairchild, D. N. Slatkin, D. Greenberg, S. Packer, H. L. Atkins, and S. J. Hannon, Melanin content of hamster tissues, human tissues, and various melanomas *Cancer Research*, vol. pp. 467–472, 1981;

R. Rox Anderson and John A. Parrish, The Optics of Human Skin *The Journal of investigative Dermatology*, vol. 77, pp. 13–19, 1981;

B. C. Wilson and S. L. Jacques, Optical reflectance and transmittance of tissues: principles and applications *IEEE Journal of Quantum Electronics*, vol. 26, pp. 2186–2199, 1990;

J. C. Russ. *The Image Processing Handbook*, CRC Press and IEEE Press, 1999.;

J. R. Parker. *Practical Computer Vision using C*, Wiley, 1994;

C. Steger, Extraction of Curved Lines from Images *13th International Conference on Pattern Recognition*, vol. 2, pp. 251–255, 1996;

B. G. Schunck, Edge Detection with Gaussian Filters at Multiple Scales of Resolution *Advances in Image Analysis*, vol. pp. 75–105, 1992;

J. S. Lim and J. S. Lim. *Two-Dimensional Signal and Image Processing*, Prentice Hall Signal Processing Series, 1989;

R. Deriche, Recursively Implementing the Gaussian and its Derivatives *INRIA Research Reports*, vol. 1993;

T. Lindeberg, Discrete derivative approximations with scale-space properties: A basis for low-level feature extraction *Journal of Mathematical Imaging and Vision*, vol. 3, pp. 349–376, 1993;

D. Eberly, R. Gardner, B. Morse, S. Pizer, and C. Scharlach, Ridges for image analysis *Journal of Mathematical Imaging and Vision*, vol. 4, pp. 351–371, 1994;

F. C. Glazer, Fiber identification in microscopy by ridge detection and grouping *Proceedings of the IEEE Workshop on Applications of Computer Vision*, vol. pp. 205–212, 1992;

C. Steger, Extracting Curvilinear Structures: A Differential Geometric Approach *Fourth European Conference on Computer Vision, Lecture Notes in Computer Science*, vol. 1064, pp. 630–641, 1996;

O. Monga, N. Armande, and P. Montesinos, Thin nets and crest lines: application to satellite data and medical images *Computer Vision and Image Understanding*, vol. 67, pp. 285–295, 1997;

J. Canny, A Computational Approach to Edge Detection *IEEE Transaction on Pattern Analysis and Machine Intelligence*, vol. PAMI 8, pp. 679–698, 1986;

J. R. Parker. *Algorithms for Image Processing and Computer Vision*, Wiley, 1997;

Math Works Inc. *Matlab Image Processing Toolbox User's Guide*, Math works Inc., 1997;

R. S. Afzal, A. W. Yu, J. J. Zayhowski, and T. Y. Fan, Single Mode, High Peak Power, Passively Q-Switched Diode-Pumped Nd:YAG Laser *Optics Letters*, vol. 22, pp. 1314–1316, 1997;

C. D. Nabors, J. J. Zayhowski, R. L. Aggarwal, J. R. Ochoa, J. L. Daneu, and A. Mooradian, High-Power Nd:YAG Microchip Laser Arrays *Optical Society of America Proceedings on Advanced Solid-State Lasers*, vol. 13, pp. xvii+391, 234–236, 1992;

J. J. Zayhowski, Microchip Lasers Create Light in Small Places *Laser Focus World*, vol. 32, pp. 73–74 & 76–8, 1996;

D. S. Watkins. *Fundamentals of Matrix Computations*, Wiley, 1991;

J. P. Fischer, J. Dams, M. H. Gotz, E. Kerker, F. H. Loesel, C. J. Messer, M. H. Niemz, N. Suhm and J. F. Bille, Plasma-Mediated Ablation of Brain Tissue with Picosecond Laser Pulses, *Applied Physics B*. 58: 493–499 (1994);

E. J. Fiskerstrand, L. O. Svaasand, G. Kopstad, M. Dalaker, L. T. Norvang and G. Volden, Laser Treatment of Port Wine Stains: Therapeutic Outcome in Relation to Morphological Parameters, *British Journal of Dermatology*, 136(3): 467–8 (1997);

S. L. Jacques, C. A. Alter and S. A. Prahl, Angular Dependence of HeNe Laser Light Scattering by Human Dermis, *Laser Life Sci*. 1: 309–333 (1987);

A. L. McKenzie, Physics of Thermal Processes in Laser-Tissue Interactions, *Phys. Med. Biol*., 35(9): 1175–1209 (1990);

J. B. Mulliken and A. R. Young. *Vascular Birthmarks—Hemangiomas and Malformations*, Saunders, 1988;

L. O. Reynolds, C. C. Johnson and A. Ishimaru, Diffuse Reflectance from a Finite Blood Medium: Applications to the Modeling of Fiber Optic Catheters, *Appl. Opt*., 15: 2059–2067 (1976);

E. L. Sebem, C. J. H. Brenan and I. W. Hunter, Design and Characterization of a Laser-based Instrument to Treat Hemangiomas Using Spectroscopic Feedback: the "Smart Scalpel", *MIT Home Automation and Healthcare Consortium Progress Report*, No. 2–4: Oct. 1, 1999;

E. L. Sebem, K. H. Lim, C. J. H. Brenan and I. W. Hunter, Design and Characterization of a Laser-based Instrument to Treat Vascular Lesions Using Spectroscopic Feedback: the "Smart Scalpel", *MIT Home Automation and Healthcare Consortium Progress Report*: May 30, 2000; and E. L. Sebem, C. J. H. Brenan, R. R. Anderson and I. W. Hunter, Design and Characterization of a laser-based instrument with spectroscopic feedback control for treatment of vascular lesions: the Smart Scalpel, *Journal of Biomedical Optics*, October 2000, Vol. 05(04), pp. 375–382.

OBJECTS OF THE INVENTION

The present invention was made in consideration of the above problem and has as its object the provision of a laser treatment apparatus with a flexible control platform that provides for accurate and non-invasive targeting and treatment using real-time feedback control for different types of procedures.

It is another object of the invention to provide a laser treatment apparatus that can be easily modified and/or programmed to perform such different types of procedures.

Other objects and advantages of the invention may in part be obvious and may in part be apparent from the specification and the drawings.

SUMMARY OF THE INVENTION

To solve the above-described problems and to achieve the objects of the invention, a Smart Scalpel system ("Smart Scalpel") according to an embodiment of the present invention may include an imaging system, a computer vision and control system, and a treatment system.

The imaging system may utilize single or plurality, monochromatic or multi-wavelength (e.g. white light) light(s) for imaging. Images may be detected by a 2-D sensor, or camera for real-time targeting and feedback on a surface, or subsurface of tissue.

The detected images may then be processed by the computer vision and control system according to a computer model of tissue properties. The computer vision and control system may include a processor (say, a general purpose computer) for executing a number of image analysis and treatment system control instructions (e.g., software applications), which may include a number of image processing, mathematical, and color detection algorithms, on the detected images (i.e., real-time measurements) from the imaging system. Expert physician knowledge may be incorporated to computer models of tissue properties in the image analysis applications, where the models are compared with these real-time measurements, and used to distinguish between normal and selected (e.g., undesirable) tissue types. For example, physio-chemical, such as histochemical and morphological, tissue properties may be measured non-invasively throughout treatment; an extrema/derivative method may be used to locate a number of selected locations of a blood vessel; a thresholding method may be used to detect hair; and a color method may be used to detect cancer tissues, or hair The image analysis and treatment control applications may further include a programming interface for programming new models and treatments. For example, the computer vision and control system may be programmed to extract features for treatment from an actual location in an image, or from an inferred location in the image (e.g., for blood vessel treatments, a treatment target may be a detected location on a blood vessel in an image; and for hair removal, a treatment target may be a selected distance away from a detected surface hair shaft, and a selected direction where the hair disappears into the skin).

The computer vision and control system may further be programmed to suppress image noise (e.g. through software filtering), improve contrast (through image processing), and subtract background details (e.g. through subtracting different images), thus, allowing target features to be enhanced in the image, which is impossible with the human visual system.

Once the position of tissue of a selected type is identified, the treatment system may be engaged to apply a spatially localized energy source to remove or modify this tissue. This imaging, analysis, and treatment targeting sequence may be repeated until all the undesirable tissue has been treated. A micromanipulator responsive to the information extracted by the computer vision and control system may be included to direct the treatment system (e.g, therapeutic energy source) to the appropriate targets.

Consistent with the analytical processing described above, treatment may be directed at or relative to specified targets. For example, in hair removal, the computer vision and control system may control the treatment system to target an inferred location of a hair follicle in a specific direction and distance from a detected hair shaft; in vessel treatment, the treatment system may be targeted at detected locations on a blood vessel directly.

The Smart Scalpel system may further allow a physician to perform a simulation or a system check before actually performing a treatment. For example, a physician may review targets identified by the system to verify that they are correct.

A further advantage of the Smart Scalpel system of the present invention is that the kinds of treatment that it can perform is not constrained by the characteristics and parameters of the treatment system (e.g., laser treatment wavelengths) as it would be in a conventional laser device that does not "aim." In other words, the concept of selective photothermolysis for target treatment is not critical to the Smart Scalpel system of the present invention. This is because the treatment system is also spatially selective.

Even though selective photothermolysis is not critical to the Smart Scalpel system for effective treatment, the computer (software) control allows the laser energy of the treatment system to be modulated during treatment to further improve its effectiveness. The computer vision and control system can control the amount of laser energy, and the on/off state of the treatment system in real-time during treatment. There are many ways to do this modulation. For example, if a laser diode is used in the treatment system, it can be electronically modulated via the laser driver. Other instruments, such as opto-electro modulators, opto-acoustic modulators, and mechanical shutters, may also be used for such modulations. Thus, the combination of imaging, computer vision, and laser treatment control allows the laser parameters to be adjusted in real-time to accommodate variations in tissue properties (spatial and temporal). For example, when the computer "sees" a larger target during treatment, it may instruct the laser to dwell at that target for a longer time, and also to shift its focusing lenses to create a larger spot size. As a result, targets on a treatment site may be treated differently depending on their respective characteristics.

With feedback on tissue properties, laser treatment is applied until a desired outcome is achieved. For example in photothermolysis of blood vessels, the laser beam dwell time and irradiance (power per unit area) can be varied to optimize the photothermal denaturization of blood in vessels.

The real-time, rapid feedback control of the Smart Scalpel system also compensates for patient movements during the treatment. In accordance with an embodiment of the invention, the imaging, analysis, and treatment are performed at a rate such that they adjust for any bodily motion. The Smart Scalpel system may further include analysis and control processes that can reliably predict bodily movements, and anticipate target positions temporally.

Additionally, the Smart Scalpel system is amenable to integration into a tele-operation system for remote surgery.

In accordance with an exemplary embodiment of the present invention, the Smart Scalpel system may be used to target and treat nevus flammus (port wine stain or "PWS") and other hemangiomas. It may utilize lights of 577 nm and 650 nm to illuminate skin tissue from the same position, polarizers at the light output, and an imaging camera. Accordingly, a combination of Orthogonal Polarization Spectroscopy ("OPS") and Optical Reflectance Spectroscopy ("ORS") may be used for non-invasively identifying blood vessels from other tissues. The ORS-OPS technique may also be used to discriminate normal vessels, untreated PWS vessels, and treated vessels from one another based on their respective reflectance characteristics, thus monitoring tissue changes throughout a treatment to optimally photo-coagulate the blood vessels.

The spectroscopic information may further be interpreted according to a line detection algorithm to identify and accurately locate the "mid-line" of the blood vessels. The line detection algorithm may be based on a method of extracting curvilinear structures to identify and locate ridge edgels, which are locus of points where the image height is locally maximal in the direction perpendicular to the line, and where the gradient vanishes. Specifically, the center of a line may be detected by locating the points where the first directional derivative in the direction perpendicular to the line vanishes, and where the second directional derivative is of a large negative value. In addition, edges may be detected by locating the points where the first derivative is locally maximal in the direction of the gradient. The width of each line point may be detected by finding the distance of edge pixels to the left and right in the direction perpendicular to the line.

In accordance with an embodiment of the invention, noise in the spectroscopic image may be removed by Gaussian smoothing prior to the line detection described above. Gaussian convolutions may be implemented using finite impulse response ("FIR") and/or infinite impulse response ("IIR") filters. In addition, the derivatives may be approximated directly from the smoothed images in accordance with a discrete scale-space theory where an image is smoothed with a large support Gaussian kernel followed by computing the derivatives using small support difference operators. Line points with high saliency may be extracted using hysteresis thresholding.

The Smart Scalpel system may also include an imaging strategy of dividing an image field into regions having equal numbers of targets in order to speed image processing and treatment operations. The imaging strategy may include the steps of: First Pass Imaging, Growing Areas from Seed Pixels, Regional Division, and Feedback Operation. During the First Pass Imaging, pixels (or "seed pixels") of the lines detected according to the method described above are marked. Then, an area of a predetermined width around the seed pixels is grown to anticipate future blood vessel positions in the image, which may be caused by motion tremor, etc. The image field is then divided into rectangular regions each containing an equal number of seed pixels.

Thus, once the position of diseased/damaged tissue is identified, a spatially localized energy source may be applied to remove or modify this tissue. This imaging and laser targeting sequence may be repeated until all the undesirable tissue has been treated.

The invention accordingly comprises the several steps and the relation of one or more of such steps with respect to each of the others, and the apparatus embodying features of construction, combination(s) of elements and arrangement of parts that are adapted to effect such steps, all as exemplified in the following detailed disclosure, and the scope of the invention may be indicated in the claims.

BRIEF DESCRIPTION OF THE DRAWINGS

FIG. 5 is a chart summarizing the types of lasers that may be used in dermatology and their specifications;

FIGS. 8A and 8B are diagrams showing methods of implementing optical polarization spectroscopy ("OPS") imaging in accordance with an embodiment of the invention;

FIG. 9 is a diagram showing light absorption levels of whole blood and melanin;

FIGS. 20A, 20B, and 20C illustrate results of image processing performed in accordance with an embodiment of the invention;

FIG. 23 is a chart summarizing process time for a particular computer processor for image processing operations of an embodiment of the invention;

FIGS. 24A, 24B, 24C, 24D, and 24E demonstrate an imaging strategy for improving image processing performance in accordance with an embodiment of the invention;

FIG. 28 is a chart listing characteristics of a laser used in accordance with an embodiment of the invention;

FIGS. 32A, 32B, 32C, and 32D illustrate imaging according to an embodiment of the invention.

DETAILED DESCRIPTION OF THE PREFERRED EMBODIMENT

Figure 1A:
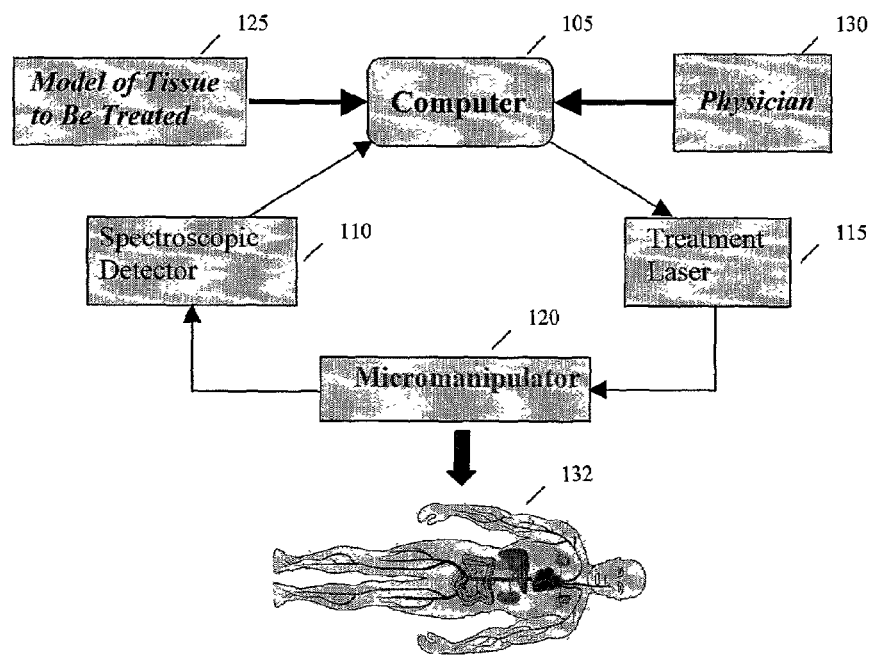
FIGS. 1A and 1B illustrate a Smart Scalpel system in accordance with an embodiment of the present invention.
Figure 1B:
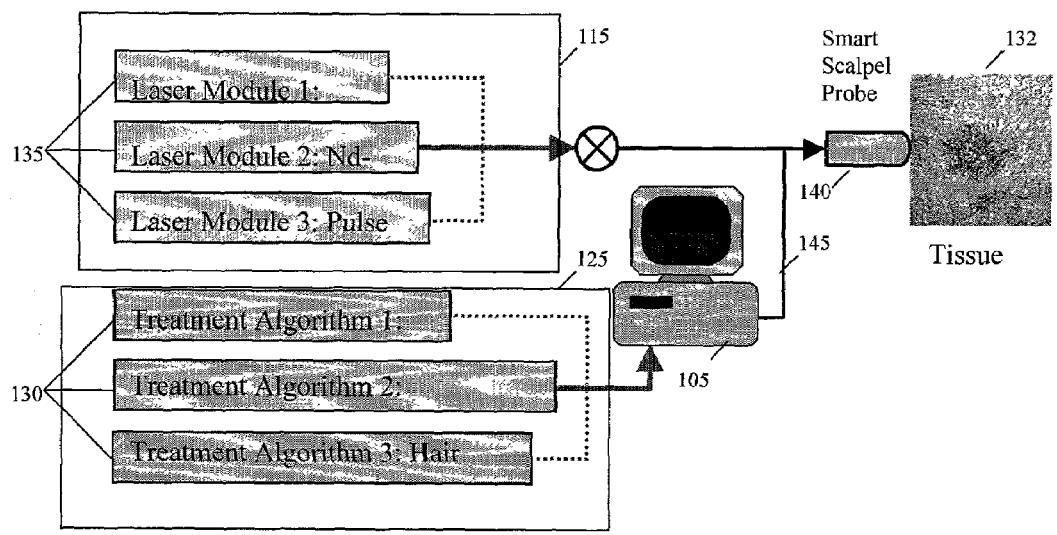

FIGS. 1A and 1B illustrate a Smart Scalpel system 100 in accordance with an embodiment of the present invention. As shown in FIG. 1A, Smart Scalpel system 100 includes a computer 105, a spectroscopic detector 110, a treatment laser 115, and a micromanipulator 120. Tissue model (physical properties) 125, as well as expert knowledge from a physician 130, describing a number of tissue attributes (e.g., those of healthy tissues versus those of diseased tissues to be excised) and/or targeting/treatment parameters may be input to computer 105. Computer 105, based on the inputted properties and/or parameters, may control spectroscopic detector 110 and treatment laser 115, which may be included in micromanipulator 120. Micromanipulator 120, which may be a handheld device, an automated apparatus, or the like, serves as an interface between a tissue volume (patient) 132 and Smart Scalpel 100, providing a convenient way to extract information about tissue state and to direct therapeutic energy to appropriate targets. For example, spectroscopic detector 110, which may be included in micromanipulator 120, may include illuminators (e.g., strobe lamps) for lighting tissue volume (patient) 132 and detectors (e.g., cameras) for detecting light reflected by tissue volume 132. The detected light may then be analyzed by computer 105 based on the inputted properties and/or parameters. Thus, Smart Scalpel system 100 may non-invasively measure the physiochemical properties (morphological, biochemical, mechanical, electrical, etc.) of tissue volume 132 and compare this information with a computer model to identify tissue types (i.e. diseased tissues or any other treatment targets). This information may then be used for continuous feedback control of the targeting and treatment of selected targets in tissue volume 132 with a spatially localized energy source, say, treatment laser 115 (which may be included in micromanipulator 120), leaving the surrounding healthy tissues intact. This automated scanning and targeting sequence may be repeated until a procedure is complete (e.g., all diseased tissues have been treated).

As illustrated in FIG. 1B, Smart Scalpel system 100 may utilize a platform technology which may include a highly modular instrument. In accordance with an embodiment of the invention, tissue model (physical properties) 125 include a library of (software) algorithms 130 that are designed for different types of procedures and a corresponding selection of laser modules 135 for performing the procedures. Micromanipulator 120 may be embodied in a probe 140, which may be coupled to laser modules 135 through optical fiber, for performing a selected procedure on tissue. A selector 145 may be controlled by computer 105 to select one of laser modules 135 for a selected procedure according to a corresponding one of algorithms 130. In this way, one single instrument can be used to perform a number of different procedures. It is noted that physician knowledge 130 may be incorporated to algorithms 130 and modules 135 and/or separately inputted at computer 105. In other words, a physician may use any one or combination of algorithms 130 and/or laser modules 135, together with any real-time programming and/or inputs at computer 105, to perform any procedure using probe 140, which may be a handheld instrument or an automated apparatus.

It is noted that Smart Scalpel system 100 may be used to perform remote surgery wherein link 145 between computer 105 and treatment laser 115 and/or probe 140 may be a remote link (wired or wireless) providing computer 105 remote control over treatment laser 115 and/or probe 140. In another embodiment of the invention, computer 105 may be connected to one or more computers (not shown) via any type of network connection(s) (not shown). Computer 105 may, thus, receive additional treatment algorithms and/or control decisions (e.g., physician input) from any computer so connected. As a result, Smart Scalpel system 100 (i.e., computer 105) may be remotely controlled using a computer that is connected thereto through any type of network connection to perform any procedure. The real-time feedback of Smart Scalpel system 100 may be forwarded to the remote computer via the network connection. Furthermore, collaborative input from multiple locations may be received by Smart Scalpel system 100 (i.e., computer 105) for performing any such procedure. For example, physicians from different locations may upload additional treatment algorithms and/or data to computer 105 that may include suggestions for treatment, new procedures, new methods of diagnosis, etc. The real-time feedback of Smart Scalpel system 100 may be forwarded to one or more remote computers via a network connection(s) at computer 105, thus, allowing one or more physicians to observe and/or participate in a procedure performed using Smart Scalpel system 100 from a remote location(s) (i.e., the physician(s) may provide real-time collaborative input, e.g., suggestions, during the procedure).

Figure 2:
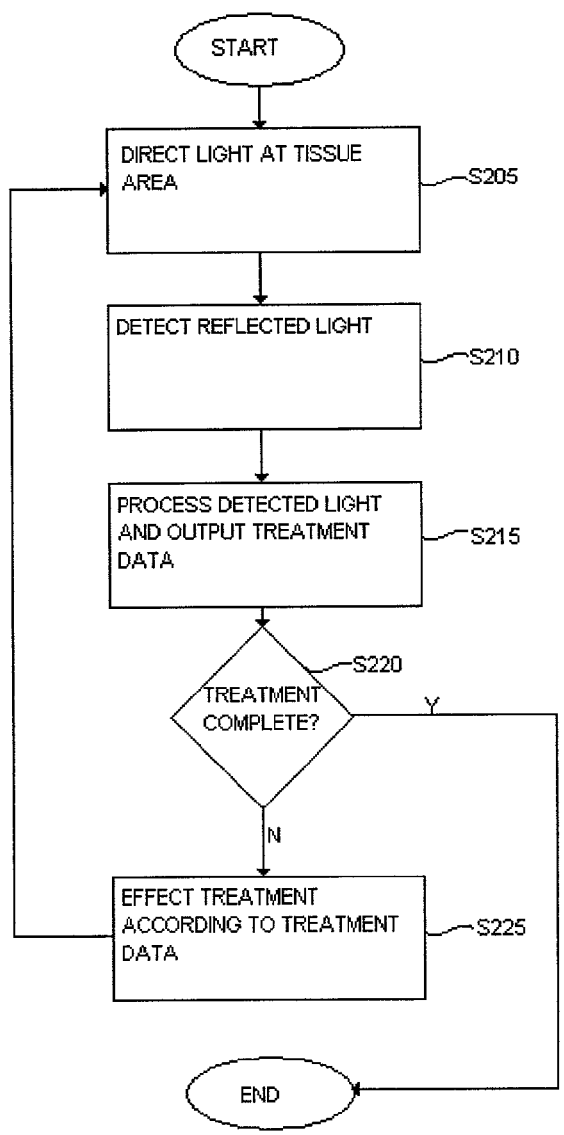
FIG. 2 shows a process for providing treatment using the Smart Scalpel system in accordance with an embodiment of the present invention.

FIG. 2 is a flowchart of a process 200 that exemplifies an algorithm that may be used with Smart Scalpel system 100 for performing a procedure.

As shown in FIG. 2, process 200 begins at step S205 by directing single or plurality, monochromatic or multi-wavelength (e.g. white light) light(s) at a tissue area. Next, at step S210, reflection(s) of the light(s) from the tissue area is detected. The detected reflection(s) thus forms an imaging of the tissue area. The image is then processed based upon predetermined conditions (e.g., a preprogrammed algorithm, real-time inputs by a physician, etc.) to generate treatment data, as shown by step S215. Treatment data may include the power and wavelength to be used for effecting treatment and the location at which the treatment laser (115) is to be directed. In addition, treatment data may include an indication of whether treatment has been completed. For example, if all of the targets in a tissue area have been treated, treatment data may output an indication of completion. At step S220, it is determined whether treatment is complete. This determination may be based upon whether treatment data includes an indication of completion. This determination may also be based upon processing of the image formed by the detected reflection(s). If it is determined that treatment has been completed in the tissue area ("Y"), process 200 terminates, at which point process 200 may be restarted at a new tissue area. If it is determined that treatment has not been completed ("N"), at step S225, treatment data is outputted, say, to treatment laser 115, for effecting treatment and process 200 returns to step S205. Thus, process 200 may be executed continuously during a treatment procedure so that treatment is effected in accordance with real-time feedback (i.e., detected reflection(s)) until a tissue area is completely treated. In addition, treatment efficacy may be continuously monitored, and treatment data may be continuously adjusted.

As an example, dermatology is an area where Smart Scalpel system 100 may be used for various types of treatment, such as the removal of nevus flammus, which includes port wine stains ("PWS") and telangiectasias, and the removal of superficial leg veins, psoriasis, and hair.

PWS is a congenital, vascular malformation of the dermis, which is estimated to occur in five children per thousand births. On a macroscopic scale, PWS appears as a pink, red, or purple lesion that commonly involves the forehead, face, occiput, and nuchal regions. Since malignant transformation does not occur, the indication for treatment is primarily based on cosmetic considerations and psychosocial stress. PWS therapy may involve the illumination of a ~10 mm diameter region of the skin with the output of a pulsed dye laser. Selective absorption of the laser energy by the blood results in thermal necrosis of blood vessels and irreversible damage. Over time the body absorbs these vessels, and the lesion fades or completely disappears. In practice, selective photothermolysis also damages the tissue surrounding the blood vessels. Since there is no discrimination between the blood vessels and healthy tissues, the collateral damage results in pain for the patient and tissue scarring. The procedure is slow and the treatment response is sometimes poor. Finally, aside from physical appearance, no feedback is generated to assess treatment efficacy or appropriateness of the photon dosage.

Therefore, in accordance with an exemplary embodiment of the present invention, rather than scanning a laser across the entire tissue, Smart Scalpel system 100 may use a blood vessel reflectance signal to identify blood vessels to be treated, and delivers laser energy only onto those vessels. In addition, this reflectance signal is monitored throughout the treatment to assess the treatment efficacy and to adjust the laser parameters (e.g., laser power and pulse width) accordingly. In a similar fashion, blood vessels or other structures can be identified and targeted with the Smart Scalpel system, and can be used both on the exterior and in the interior of a patient. For instance, blood vessels on other structures in tumors or other undesired growths, such as heart, lung, stomach, colon, intestinal, breast, or brain tumors and the like can be targeted with the Smart Scalpel system and the system can thus be used in surgical treatments. The system can also be used for removing unwanted hair, e.g., by targeting the root of a follicle.

As described before with reference to FIG. 1B, any laser (135) coupled to Smart Scalpel system 100 via optical fiber may be used. Therefore, a dermatologist can have the flexibility to use a laser wavelength he/she deems fit. For more effective treatment, Smart Scalpel system 100 may also be designed to recognize dimensions of blood vessels in real-time in order to utilize an optimal laser dosage.

As may be described in further detail below, major design components of the PWS Smart Scalpel of the exemplary embodiment are (1) a non-invasive method to selectively identify and locate blood vessels within the PWS, (2) a means to deliver laser energy to targeted spatial locations, (3) a strategy for heating blood vessels within the PWS volume imaged, and (4) a method to estimate the optimal laser dosage during treatment. Smart Scalpel system 100 aims for high spatial resolution to see fine blood vessels, and high bandwidth to eliminate problems associated with relative motion between instrument 140 and tissue volume (patient) 132.

Tremor has been identified as the highest frequency source of motion between Smart Scalpel system 100 and tissue volume (patient) 132. Tremor is an approximately rhythmic, roughly sinusoidal involuntary movement. It may be either pathologic or physiologic; physiologic tremor is a normal variant that happens in every person. Tremor is also classified on the basis of when it occurs, i.e., either with a certain posture, at rest, or during action. A resting tremor occurs when the person is attempting to maintain the position of a body part at rest, e.g. when the limb is fully supported against gravity and the muscles are not voluntarily activated. In this case, the frequency is commonly between 3 to 6 Hz. Physiological resting tremor (3 to 6 Hz) is identified as the main type of patient tremor during laser treatment. However, it may be increased by emotions such as anxiety, fear and stress, or physical pain. During laser treatment with Smart Scalpel system 100, probe 140 may be held securely against tissue volume (patient) 132. This may restrict relative motion since the probe may move together with the body. In addition, the patient may be in a resting posture with the body supported, or even constrained to restrict movement. With these measures implemented together, it is thus reasonable to assume that the maximum frequency is approximately 3 Hz. The tremor displacement can also be deduced from measured tremor amplitudes. A suitable value of the displacement found may be 370 µm.

Nyquist Sampling Theorem states that no information is lost if a waveform of highest frequency v is sampled faster than the Nyquist frequency, where $$f_{Nyquist} = 2v. \quad (1)$$

Therefore, if the tremor frequency is approximately 3 Hz, then Smart Scalpel system 100 should ideally be sampling at a minimum frequency of 6 Hz (system bandwidth).

Vascular Lesions

PWS represents one type of congenital malformation involving mature capillaries. These "hemangiomas" are members of a larger group of congenital lesions termed nevus flammeus, which commonly involve the forehead, face, occiput, and nuchal regions.

Optically, skin can be considered to consist of four distinct layers: the epidermis, the upper dermis layer, the lower dermis layer, and the subcutaneous fat.

The epidermis is approximately 100 µm thick and is composed of closely packed epithelial cells forming microscopically distinct layers. The cells on the surface of the skin, forming the horny layer (stratum corneum), are fully keratinized dead cells. Beneath the epidermis, the upper dermis layer (400 µm thick) contains a system of capillary loops. The capillaries are supplied by the superficial arteriolar plexus formed by vessels 50 µm in diameter (in normal skin), which in turn originate from arteries entering the lower dermis. This superficial plexus is one of the primary factors in skin coloration. The lower dermis (400 µm) is composed of collagen bundles, elastic tissue, sweat glands, follicular structures, and blood vessels. Beneath the lower dermis is the subcutaneous fat. The major absorbing or scattering entity in each layer is melanin, blood and collagen.

PWS consists of a large number of ecstatic blood vessels (capillary-to-venule sized) in the superficial dermal capillary, resulting in a bluish-red skin blemish. The pathological structure of PWS can be classified into four group types: constricted, intermediate, dilated and deeply located.

In the constricted type, the blood vessels differ little from the normal pattern, and their number is not more than in normal skin. In the dilated type, the vessels are considerably enlarged (up to 400 µm) and often contain red cells. In some cases, this alteration in the vessels is found scattered throughout the upper and lower dermis (deeply located type). The intermediate type shows histological features common to the constricted and dilated types.

PWS blood vessels can enlarge with age. If left untreated, they may become enlarged and elevate the skin, causing the surface to take on a cobblestone appearance. Occasionally, the vessels can create "exaggerated growth" or hypertrophy, which can lead to impairment of functions such as seeing and breathing.

Figure 3A:
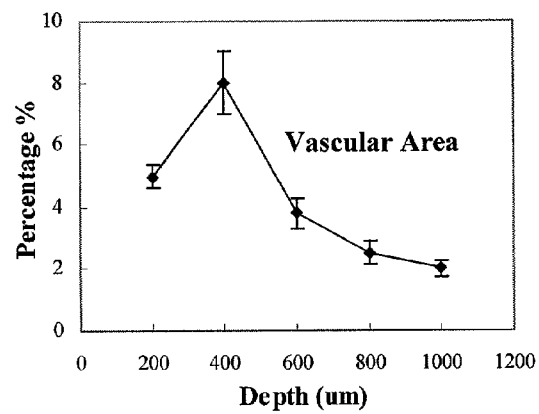
FIGS. 3A and 3B illustrate characteristics of Port Wine Stains ("PWS")
Figure 3B:
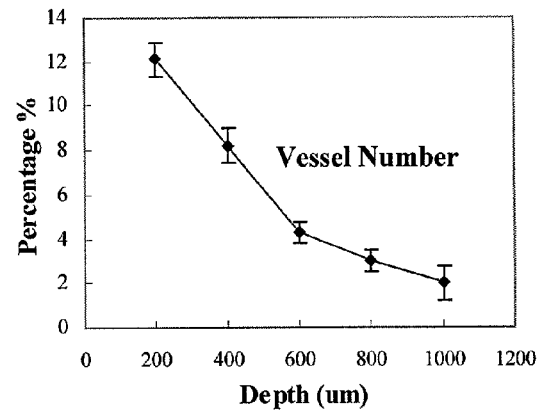

The central abnormalities characterizing PWS are an increase in vessel number (vascular profiles) and ectasia. FIGS. 3A and 3B illustrate characteristics of PWS in a study involving 100 patients. "Vascular area" in FIG. 3A refers to the percentage of dermal area composed of blood vessels.

As shown by the results in FIG. 3B, vessel number sharply decreases with depth and the majority of vessels are located in the immediate sub-epidermal dermis. The mean vessel depth is 460±170 µm, with a median depth of 310 µm. This means that the penetration depth of an imaging light and treatment laser may reach beyond 310 µm for the treatment to be effective.

The graphs also revealed that the vascular area at most depths are below 8%. This means that healthy tissue actually make up the majority of the PWS region, unless the blood vessels at different depths crisscross so much that the effective area becomes large. Therefore, the current treatment method of illuminating the entire region with laser is very inefficient since only a small percentage of the region needs to be treated. This observation serves to reinforce the need for an automated instrument that only targets blood vessels.

During laser exposure, absorption and radiationless deexcitation convert radiant energy into heat within each target in the exposure field. Essentially, any mammalian tissue heated to 70° C. to 100° C. would suffer protein denaturation, leading to "coagulation necrosis". Coagulation necrosis is useful for causing hemostasis due to the denaturation of plasma proteins and the closing of vessels. The vessels then collapse and are reabsorbed by the body, which results in lesion blanching.

Using appropriate dosimetry, laser treatment of PWS can achieve "selective photothermolysis", which induces selective thermal damage of abnormal blood vessels and minimizes the risk of scarring. Although results of clinical studies are encouraging, a study in 1997 showed that only a small proportion of patients (10–20%) obtained 100% fading of their PWS, even after undergoing multiple treatments. Due to the complexity of PWS pathology, it is difficult to use one set of laser treatment parameters to treat all types of PWS lesions. Therefore, Smart Scalpel system 100 of the present invention allows for user-specified selection of irradiation parameters. As a result, the optimal parameters can be selected based on the anatomy and physiology of the PWS.

The three main parameters necessary to achieve selective photothermolysis are (1) a wavelength that is preferentially absorbed by the desired targeted structure, (2) sufficient laser fluence (energy per unit area in J*cm$^{-2}$) to reach a damaging temperature in the targeted structure, and (3) an exposure duration less than or equal to the thermal relaxation time of the target.

The optimal laser wavelength $\lambda_L$ is defined as the wavelength that maximizes the number of blood vessel damage and penetration depth, while leaving the epidermal-dermal junction undamaged. This wavelength should result in substantial hemoglobin absorption and minimal scattering and absorption by other tissues.

Figure 4:
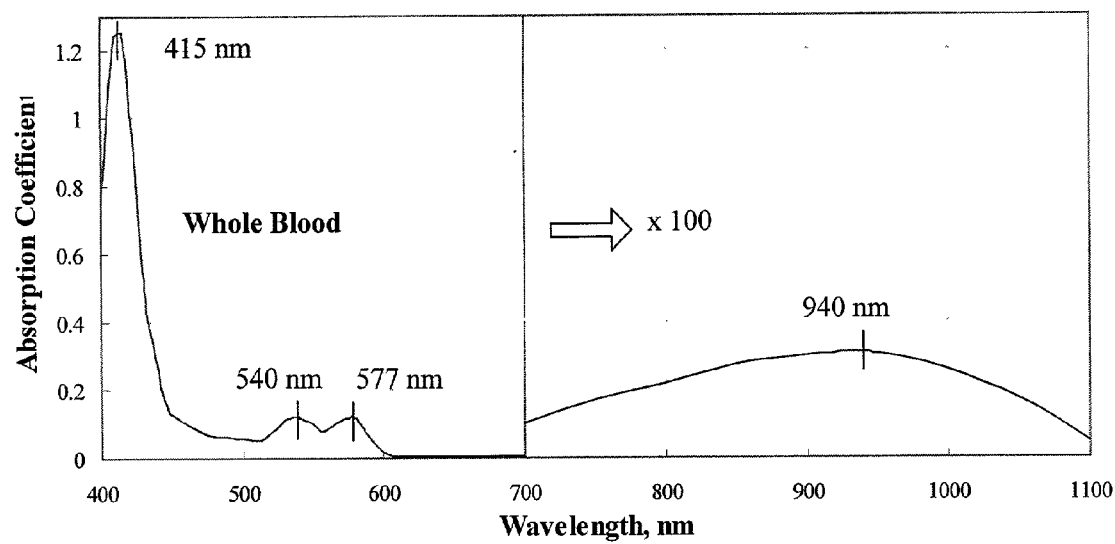
FIG. 4 is a graph illustrating the absorption coefficient of whole blood at various wavelengths of light.

In general, $\lambda_L$ should coincide or be close to an absorption spectral peak of hemoglobin. As shown in FIG. 4, there are four major absorption peaks in the visible to IR region at 415 nm, 540 nm, 577 nm and 940 nm. These wavelengths are centered at an isobestic point of oxy- and deoxy-hemoglobin (whole blood).

The higher the absorption coefficient, the greater the degrees of energy transfer. However, the depth of tissue penetration is also an important factor. Scattering probability by tissue varies as $1/\lambda^4$ (Rayleigh scattering), and major tissue chromophores tend to have greater absorption at shorter wavelengths. Therefore, longer wavelengths have greater penetration depths. For this reason, despite the fact that 415 nm has the greatest blood absorption, there is too much scattering for the photons to reach most blood vessels. Most of the popular treatment wavelengths currently used in clinics lie around the two middle absorption bands.

Current clinical applications also use wavelengths near the fourth absorption band, such as an Nd:YAG laser at 1064 nm. Such lasers are used for treating deep vessels, and since the hemoglobin absorption is lower at those wavelengths, the laser energy may be greater for effective heating.

It is important to know the damage threshold fluence sufficient to effect selective photothermolysis. The laser fluence (J/cm$^2$) is difficult to establish by theoretical modeling because of epidermal melanin absorption, multiple scattering events within the skin, and the fact that blood vessels are located at different dermal depths. In general, treatments using fluence of 4 to 8 J/cm2 are used for vascular lesions. FIG. 5 gives a summary of the types of lasers in dermatology and their specifications.

Current pulsed lasers do not interface with an external trigger source for pulse control. On the other hand, the pulse width of CW lasers can be easily controlled using optical modulators or deflectors, which can be integrated into Smart Scalpel system 100.

The pulse duration governs the spatial confinement of the thermal energy within the targeted vessel. Ideally, the pulse duration $T_p$ should be compatible with the diameter d of the vessel and be about equal to the thermal relaxation time $T_d$ for that dimension. The thermal relaxation time, defined as the time required for the instantaneous temperature generated inside the blood vessel after exposure to the laser pulse to decrease by 50%, is given by:

$$\tau_r = \frac{d^2}{16\alpha}, \quad (2)$$

where α is the thermal diffusivity. For blood composed of approximately 70% water, the thermal diffusivity a is 1.2× 10$^{-7}$ m$^2$/s. Therefore, typical values for $\tau_r$ are ≈1 ms for d=50 μm and ≈10 ms for d=150 μm. These values are in agreement with measured 1 to 10 ms pulse width requirement.

If $T_p >> T_r$, heat diffuses outside the vessel during the laser exposure, reducing the target specificity, and can cause extra thermal damage to surround tissue. A very short pulse, $T_p << T_r$, may generate a high-peak intravascular temperature rise, leading to localized explosive vaporization of tissue water, or to photoacoustic shock waves, which may result in vessel rapture. Hemorrhage leading to purpura then takes place, and in most cases, repair mechanisms may revascularize the tissue since the vessels are not completely obliterated. In the ideal situation where $T_p \approx T_r$, the thermal energy is just enough to diffuse to the vessel wall and coagulate it. Here, selective photothermolysis takes place where the blood vessels "cook" to result in tissue necrosis and collapse.

Long exposure times generally treat large vessels (while sparing the small ones) and vice versa. For more effective treatment, Smart Scalpel system 100 is designed to recognize the diameter of the blood vessels during treatment and adjust the laser pulse width in real time. This capability is very important, and is impossible to implement with the current treatment techniques.

Tissue Optics

In order to design the optical system of Smart Scalpel system 100 for the treatment of PWSs, it is important to understand the interactions between light and skin tissues.

Figures 6, 7:
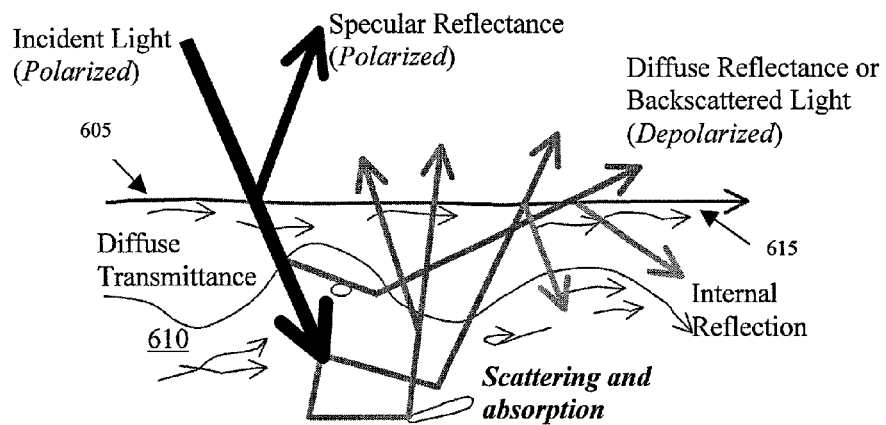
FIG. 6 illustrates the components of light-tissue interaction at a tissue interface.
FIG. 7 is a chart summarizing optical properties at 633 nm derived from a diffusion theory.

As illustrated in FIG. 6, there are four components of light at a tissue interface: (1) specular reflectance arising from a skin surface 605, (2) diffuse reflectance due to light backscattered from within tissue 610, (3) diffuse transmittance in tissue 610, where absorption and scattering take place, (4) internal reflection of scattered light that strikes an interior surface 615 of tissue 610.

A small fraction (4 to 7%) of an incident radiation is reflected from skin surface 605 due to the change in refractive index between air ($n_d$=1.0) and the stratum corneum ($n_d$≈1.55). Skin surface is not continuously flat, but contains multiple folds with air spaces between them. Therefore, these surfaces present additional optical interfaces for specular reflectance. Taken together, these specular reflections account for a "glare" from skin and contain the visual cues related to surface texture. It may be necessary to eliminate this "glare" (or "noise") during imaging.

The light that is not initially reflected enters tissue 610, where it is absorbed and/or scattered. Scattering causes a change in the direction of light propagation, and is the only physical process by which this light can be returned through skin surface 605 to participate in skin reflectance. The backscattered light component carries all visual cues related to internal skin structures such as blood vessels or infiltrates, but carries few or no visual cues related to the surface texture.

Skin tissues are a highly turbid medium and photons undergo many scattering and absorption events as they travel though skin tissues. Scattering results from physical inhomogeneities in a medium, which leads to inhomogeneities in the refractive index. The scattering and absorption processes taken together essentially determine the penetration of radiation into the skin, as well as the remittance of scattered radiation from the skin.

Three main optical parameters that govern the behavior of light-tissue interaction are the scattering coefficient $\mu_s$, absorption coefficient $\mu_a$, and anisotropy coefficient g, which is a measure of the asymmetry of the single scattering pattern. From here, the reduced scattering coefficient $\mu_s'=\mu_s(1-g)$, which describes the forward scattering fight loss, and the total optical extinction coefficient $\mu_t=(\mu_s+\mu_a)$ can be calculated. The reciprocal of the total optical extinction coefficient is sometimes referred to as the transport mean free path (MFP), or the distance that a photon travels before being scattered:

$$MFP = \frac{1}{\mu_a + \mu_s(1-g)}. \quad (3)$$

These optical properties at 633 nm (derived from a diffusion theory) are summarized in FIG. 7.

The epidermis has greater scattering and absorption coefficients of $\mu_s \approx 47$ mm$^{-1}$ and $\mu_a \approx 1.9$ mm$^{-1}$ respectively. In a multi-layer model of the skin tissue, it is normally assumed that $\mu_s$ is the same for both the epidermis and dermis. This assumption is justified because, firstly $\mu_s$ does not vary drastically between most tissue types at the same wavelength, and secondly the epidermis is much thinner than the dermis. Therefore, it is often further assumed that the optical extinction coefficient $\mu_s$ of the tissue has a single value (homogeneity).

Specular reflectance can be reduced to values within the range for normal skin by applying index matching compounds capable of spreading to and filling the spaces in the skin. These index matching compounds may have $n_d$ close to that of the stratum corneum, exhibit flat transmission spectrums, and have low absorptions.

Another important observation is that the decrease in skin reflectance is unrelated to optical absorption by the applied compounds since they have low absorption coefficients. Therefore, a greater fraction of the incident radiation may now penetrate the plaque.

As shown in FIG. 6, multiple scattering scrambles the polarization of a polarized incident light, and specular reflectance preserves the polarization plane of the incident light. Therefore, viewing skin through a linear analyzer separates the two components of tissue reflectance. When the planes of polarization are parallel, images with enhanced surface details may be obtained and these may be useful for examination of texture, elevation and scale. When the polarization planes are orthogonal, only depolarized photons scattered within the tissue can pass the analyzer, and an enhanced view of vasculature, inflammatory and pigmented lesions is obtained. Thus, orthogonal polarization spectroscopy ("OPS") produces high contrast images otherwise inaccessible by standard intravital microscopy techniques.

FIGS. 8A and 8B each illustrate a method of implementing OPS imaging. Total elimination of the specular component is achieved when a polarizer filter 805 and an analyzer filter 810 (for a light source 815 and a camera 820, respectively) are arranged at right angles to each other. This is because the polarization plane of the incident light is parallel to the plane of analyzer 810.

It should be noted that the oblique lighting shown in FIG. 8B may produce unwanted shadows (e.g., 823) from the raised or depressed surfaces on an object 825.

Optical reflectance spectroscopy ("ORS") uses diffused white-light irradiation to detect backscattered (reflected) light from PWS skin at visible and near-infrared wavelengths. The reflected spectrum at specific wavelengths contains information of a lesion, and is dependent on the skin optical and anatomical properties.

ORS combined with OPS may be used in Smart Scalpel system 100 to non-invasively identify blood vessels from other tissues in the PWS. The PWS (and skin in general) contains two dominant chromophores: melanin resident in the epidermis and hemoglobin found in the blood. FIG. 9 shows that whole blood exhibits two strong absorption bands at 540 nm and 577 nm due to a high concentration of hemoglobin chromophore. The other two absorption peaks are at 415 nm and 940 nm. In comparison, the relative melanin absorption spectrum generally decreases with increasing wavelength, while its overall magnitude scales with melanin concentration.

From FIG. 9, it can be seen that normalization of the absorption spectrum at 577 nm (where blood absorption dominates) with respect to the melanin spectrum at 650 nm (where melanin absorption dominates) generates a high contrast spectrum. Therefore, subtraction (or ratio) of PWS images taken at these two wavelengths generates a high contrast image from which blood vessels are uniquely identified and their locations determined.

In addition to absorption, the scattering properties of skin may be considered in the selection of an appropriate imaging scheme. In general, longer wavelength lights are highly forward scattering, thus allowing both substantial penetration of light into tissue and high remittance of light scattered out of the tissue after penetration. Therefore, although the greatest hemoglobin absorption peak is at 415 nm, this wavelength is too short to penetrate to the depth of PWS blood vessels. At 415 nm, the penetration depth, defined as the distance at which the energy incident on the skin is extinguished by 37% (1/e), is 100 μm. On the other hand, the penetration depth of 600 nm light is approximately 550 μm, which is close to the mean vessel depth of PWS.

Figure 10:
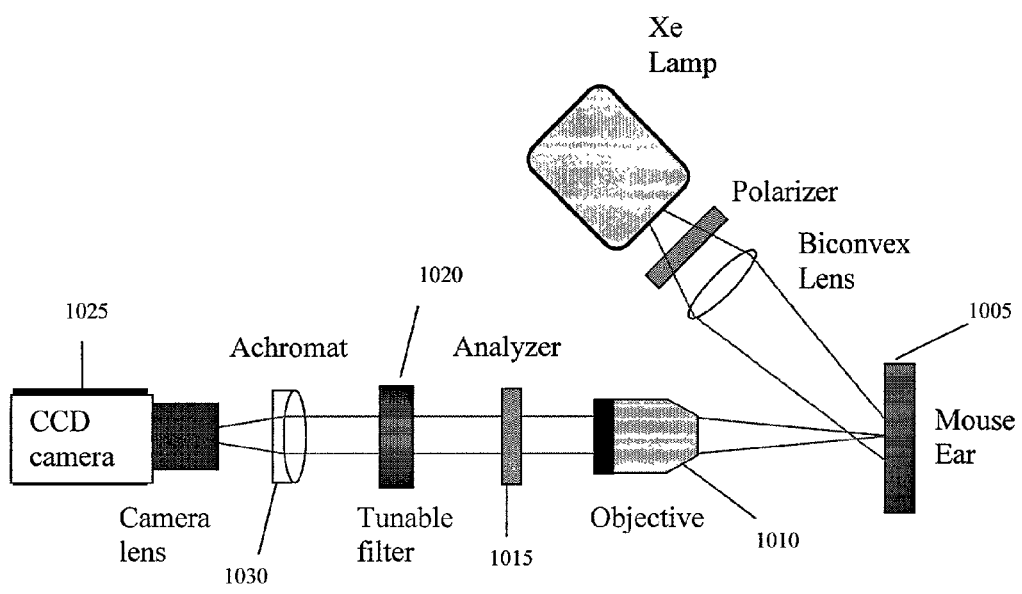
FIG. 10 shows an imaging system in accordance with an embodiment of the invention.

An optical system 1000 according to the concept discussed above is illustrated in FIG. 10. In FIG. 10, the back of a mouse ear 1005 is imaged to illustrate the concept. Polarized light may be focused on the skin surface of mouse ear 1005 and the reflected light may be collected by an objective (0.4 NA, ∞-corrected, 10×) 1010 that collimates the light and passes it through an analyzer 1015. The light may be then passed through a liquid crystal tunable filter (CRI Varispec tunable filter, VS-05/30-HC-20-S) 1020. The wavelengths used may be 577 nm for the blood vessel image and 650 nm for the normalization image (FWHM 40 nm). The light that exited the tunable filter may be focused onto a CCD camera (Pulnix TM-9701) 1025 by an achromat 1030 to minimize aberration.

Figure 11A:
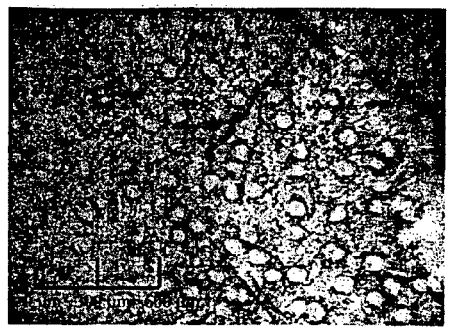
FIGS. 11A, 11B, and 11C illustrate the blood vessel contrast enhancement made possible by the imaging system of FIG. 10.
Figure 11B:
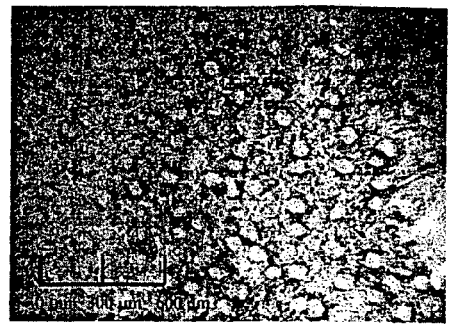
Figure 11C:
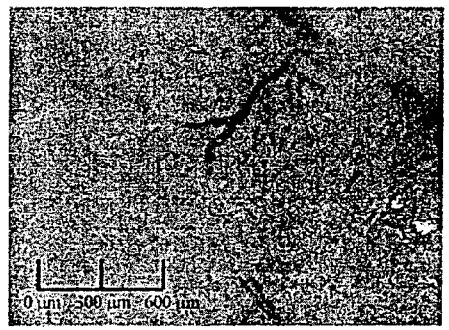

FIGS. 11A, 11B, and 11C show the blood vessel contrast enhancement made possible with this two-wavelength imaging scheme. FIG. 11A is the image of the mouse ear taken at the blood absorption wavelength of 577 nm. Besides the presence of the blood vessels, the circular hair follicles are also clearly visible. FIG. 11B is an image of the same region acquired with non-absorbing 650 nm light, and FIG. 11C is the image after background subtraction and dynamic range expansion. There is a high degree of background suppression in the image of FIG. 11C, resulting in an enhanced blood vessel image contrast. The signal-to-noise ratio ("SNR") increases by approximately an order of magnitude (SNR 0.66 to 8.34) from FIG. 11A to FIG. 11C (The definition of SNR is given in Equation (6.30) described below).

The background subtraction in FIG. 11C can be performed by either one of the following pixel operations before dynamic range expansion:

$$I_C(x, y) = \frac{I_A(x, y)}{I_B(x, y)}, \text{ or} \tag{4}$$

$$I_C(x, y) = I_A(x, y) - I_B(x, y). \tag{5}$$

In general, both methods yield almost the same high contrast image, but sometimes one of them produces a better contrast than the other. The disadvantage of the ratio method is that it is slower and more difficult to implement.

Figure 12:
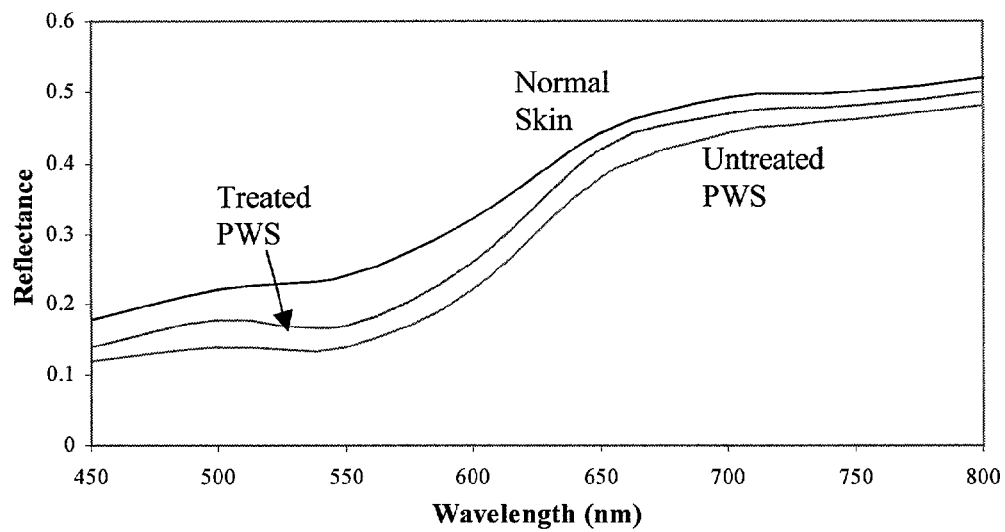
FIG. 12 shows measured reflectance spectra of normal skin and untreated and treated PWS.

ORS-OPS can be used to determine quantitatively the degree of PWS blanching following each laser treatment. Most importantly, ORS-OPS can also be used to discriminate treated PWS vessels from untreated ones. FIG. 12 shows measured reflectance spectra of normal skin and untreated and treated PWS. As illustrated in FIG. 12, there are characteristic differences in their spectra which enable easy distinction. Therefore, the treatment efficacy can be assessed in real time during the treatment process to determine whether the laser therapy is successful. Those blood vessels that are identified as successfully treated may not need to be treated again, while others that are less successful may be re-applied with the laser.

Smart Scalpel Design

The optical designs and instrumentations of Smart Scalpel system 100 according to an exemplary embodiment will now be discussed.

Figure 13:
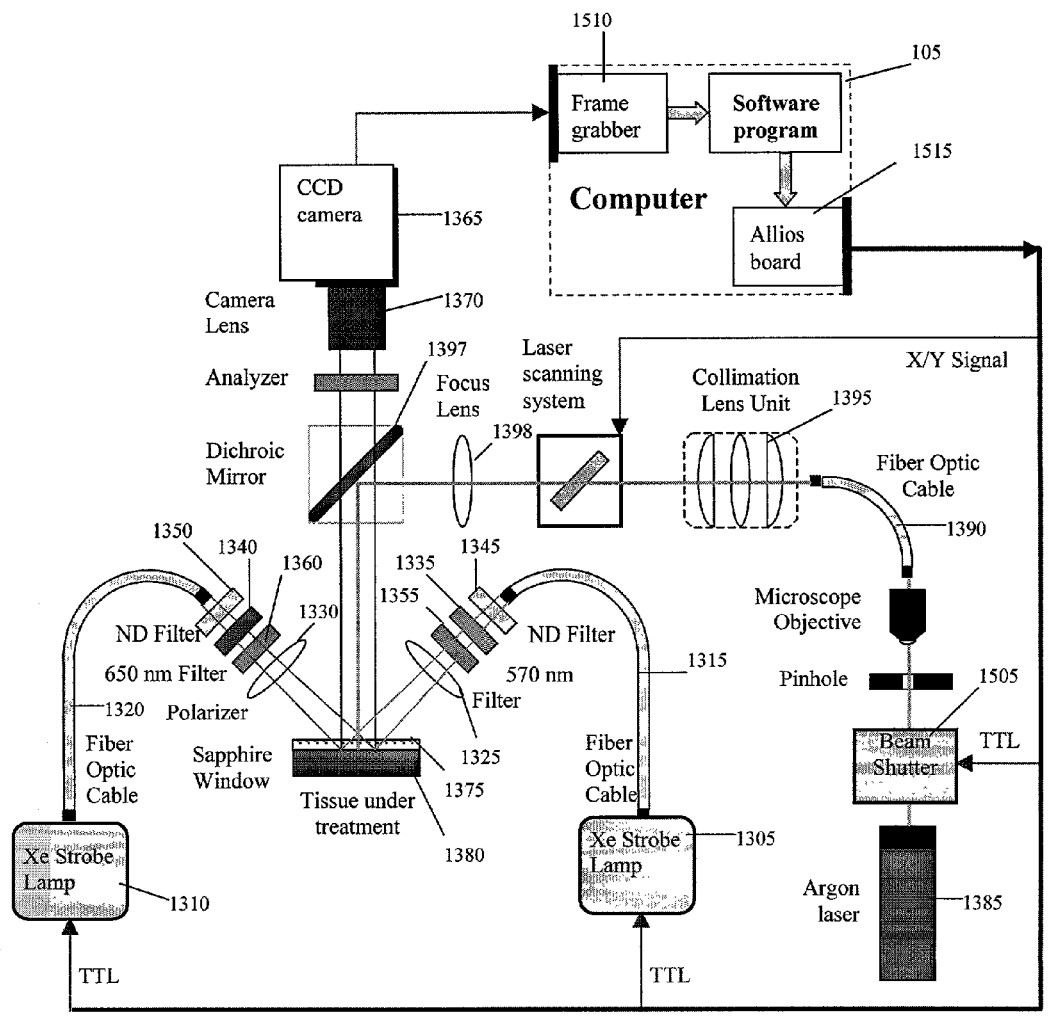
FIG. 13 is a diagram illustrating an optical design and instrumentation of the Smart Scalpel system in accordance with an embodiment of the invention.

The optical and instrumentation setup of the exemplary embodiment is shown in FIG. 13. To achieve high frequency switching, 2 Perkin-Elmer strobe lights (MVS 7020) may be used as respective illuminators 1305 and 1310. These may be fiber optically coupled strobes with a bandwidth of 20 Hz, and both the flashing and intensity can be controlled with external triggers (not shown). Large optical fibers (Dolan-Jenner, 12.7 mm diameter) 1315 and 1320 may be used to deliver the light from illuminators 1305 and 1310, which may be then focused using convex lenses 1325 and 1330 respectively.

As further shown in FIG. 13, a green filter 1335 with a 577 nm bandpass and a red filter 1340 with a 650 nm bandpass (FWHM≈60 nm) may be used to filter lights from fibers 1315 and 1320, respectively. Neutral density filters ("ND") 1345 and 1350 may be used to match the intensities from both channels. To implement OPS, polarizers 1355 and 1360 may be placed at the optical fiber exit and at CCD camera 1365. CCD camera 1365 may be a Pulnix TM-9701 with a resolution of 755 by 484 pixels and a frame rate of 15 frames per second. Camera lens 1370 may be a 55 mm computar lens (f2.8), which may be set at maximum magnification to give a field of view of 17 mm by 13 mm.

To ensure that the object may always be at the same distance to camera 1365, a sapphire window 1375 may be positioned at the focus distance, and object to be imaged (i.e., time under treatment) 1380 would be held against it. Due to its excellent material properties and hardness, sapphire window 1375 may be very thin (1 mm thick), and have a high energy threshold.

As shown in FIG. 13, oblique lighting may be used to illuminate object 1380 directly. This lighting scheme may not totally eliminate specular reflection due to less efficient polarization, and it may also suffered the disadvantage of producing shadows. This may be a problem especially during two-wavelength image subtraction because shadows created by light sources 1305 and 1310 from opposite sides may be different.

Figure 14:
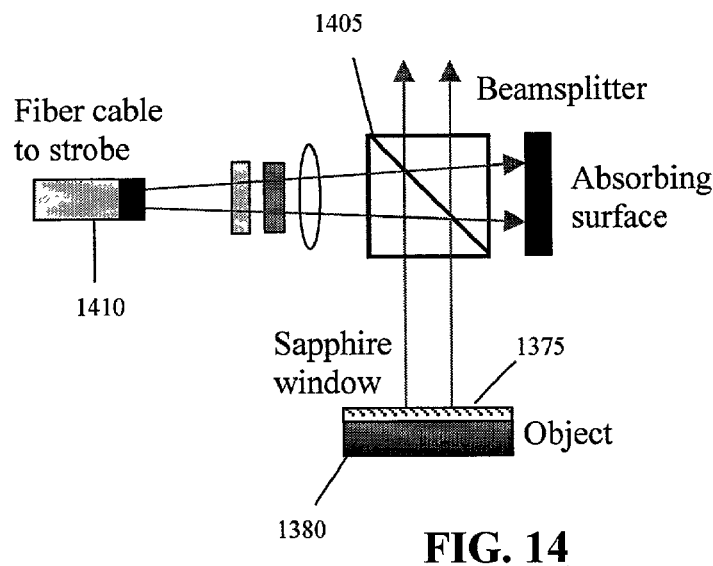
FIG. 14 illustrates the use of a beamsplitter for lighting an object according to an embodiment of the invention.

FIG. 14 illustrates the use of a beamsplitter 1405 for lighting object 1380. This arrangement may address the oblique lighting shadow issue described above. However, this arrangement may also have a problem of sapphire window 1375 reflecting a ghost image of the light source (in this case, the face of optical fiber 1410) onto camera 1365. The only way to eliminate this reflection may be to implement oblique illumination so that the unwanted reflection may be out of the field of view of camera 1365. In comparison, a benefit of using oblique lighting may be that most of the incident light intensity may be not lost, whereas a beamsplitter may lose 75% of the intensity.

Treatment laser 115 may be designed so that laser 135 can be coupled to Smart Scalpel system 100 via an optical fiber 1390. This would allow Smart Scalpel system 100 to operate as an independent unit not influenced by the location of laser source 1385. A collimation lens unit 1395 may be set up to collimate the light that spreads from the end of optical fiber 1390. The collimated beam may then pass through a two-axis galvanometer system 1397, which directs the beam towards tissue 1380 (e.g., blood vessels) in the field of view. This arrangement may convert a mirror rotation at galvanometers to a linear displacement of a laser spot on tissue 1380 (the surface of an object). Final focusing may be done using a planar-convex lens 1398. The diameter of the focused beam may be close to that of blood vessels in order to limit collateral damage.

Laser 1385 may be a 514 nm CW argon laser (Coherent Inc.) reflected directly into Smart Scalpel system 100 using mirrors. A polarizing beamsplitter (92% reflectance for S-polarization) may be then used to reflect the laser onto tissue 1380; the P-polarized laser may be converted to S-using a half-wave plate in order to achieve maximum reflection. However, if an optical fiber is later incorporated in Smart Scalpel system 100, the laser that emerges from the fiber may be depolarized. A significant amount of energy may be lost to polarize the laser again before entering the beamsplitter. An ordinary 50T-50R beamsplitter cube would also not solve the energy loss problem.

A solution may be found by using a dichroic mirror (1397) as the beamsplitter. The dichroic mirror chosen may be a high pass transmission filter with a cutoff wavelength at 540 nm. This may ensure that all the laser energy (<540 nm) may be reflected, while the 2 illumination wavelengths (>540 nm) may be all transmitted.

Although energy may be conserved, the use of dichroic mirrors may suffer from the disadvantage that laser wavelengths around the 2 illumination wavelengths (from 547 nm to 680 nm) cannot be used. This problem may be made worse by the fact that most of the popular treatment lasers used today have wavelengths within this range. For this reason, laser source 1385 may be an Nd:YAG laser. This laser operates at the infrared-red region of 1064 nm, and is excellent for treating deep vessels.

Reasons for conserving energy may include the following:

1. high energy fluence may be required for short exposure times (having a short pulse width may also increase the system bandwidth);

2. there may be energy loss at the optical fiber entry since the fiber core diameter may be small compared to the incident laser beam diameter; and 3. there may be energy loss while collimating the laser that exits from the fiber because of the large numerical aperture of the optical fiber.

If a very high power laser is available, then all the energy losses can be tolerated. In this case, a 50T-50R beamsplitter is the best option.

In order to produce the desired pulse width during treatment, an optical shutter 1505 may be used to block the laser beam. During the galvanometer transit time between targets, the shutter may be also used to prevent heating of the healthy tissue between blood vessels. Four different shutter instruments can be used.

(1) Electro-optic modulator. The electro-optic modulator has a high bandwidth and works by using the birefringence properties of a liquid crystal to alter the polarization of a beam.

(2) Acousto-optic modulator. The acoustic modulator uses compressions and rarefactions associated with an acoustic wave to form a grating that diffracts the incident light.

(3) Mechanical shutter. The energy threshold for the shutter blades may be able to withstand the high intensity laser energy.

(4) Beam deflectors. The beam deflector can be used as a shutter by deflecting the laser beam towards or away from the optical fiber. The deflector can be a mechanical galvanometer, or an electro-optic deflector, which has a much higher bandwidth.

Figure 15:
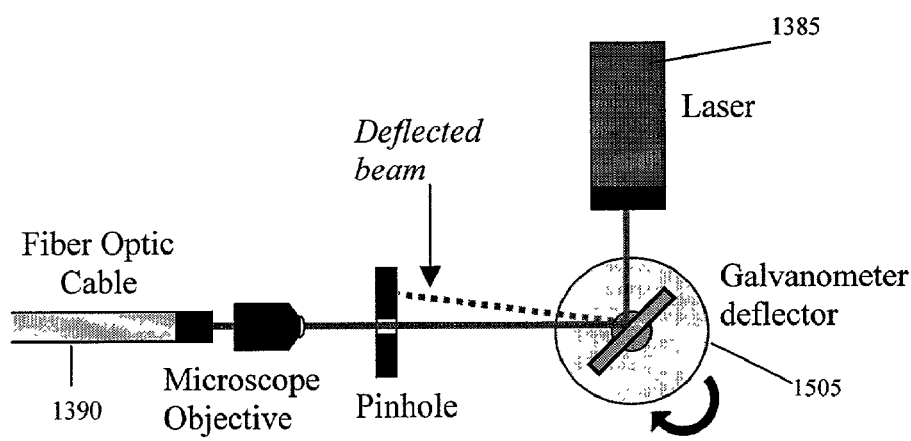
FIG. 15 shows the use of a mechanical galvanometer in the Smart Scalpel system according to an embodiment of the present invention.

As shown in FIG. 15, a mechanical galvanometer 1505 may be used in Smart Scalpel system 100 according to an embodiment of the present invention. As a result, Smart Scalpel 100 may suffer no energy loss, and 100% power modulation may be achieved.

Referring back to FIG. 13, images from camera 1365 may be acquired by a framegrabber (Matrox Meteor I1 Digital) 1510. The information acquired may be processed by computer 105, which determines blood vessel targets and feeds the coordinates to scanning galvanometers (i.e. beam shutter) 1505 via a digital-analog converter (50 kS/s @ 18 bits/sample) on a data acquisition board (Allios board, MIT Bioinstrumentation Lab) 1515. Computer 105 may also coordinate the strobing (and intensity) sequences, the optical shutter, and the feedback control loops.

With consideration for miniaturization of system 100, a miniaturized system may consist of a handheld probe. This probe may be small and light for ease of use and accessibility to all parts of the body. Therefore, the number of components inside the probe may need to be kept to a minimum.

Figure 16:
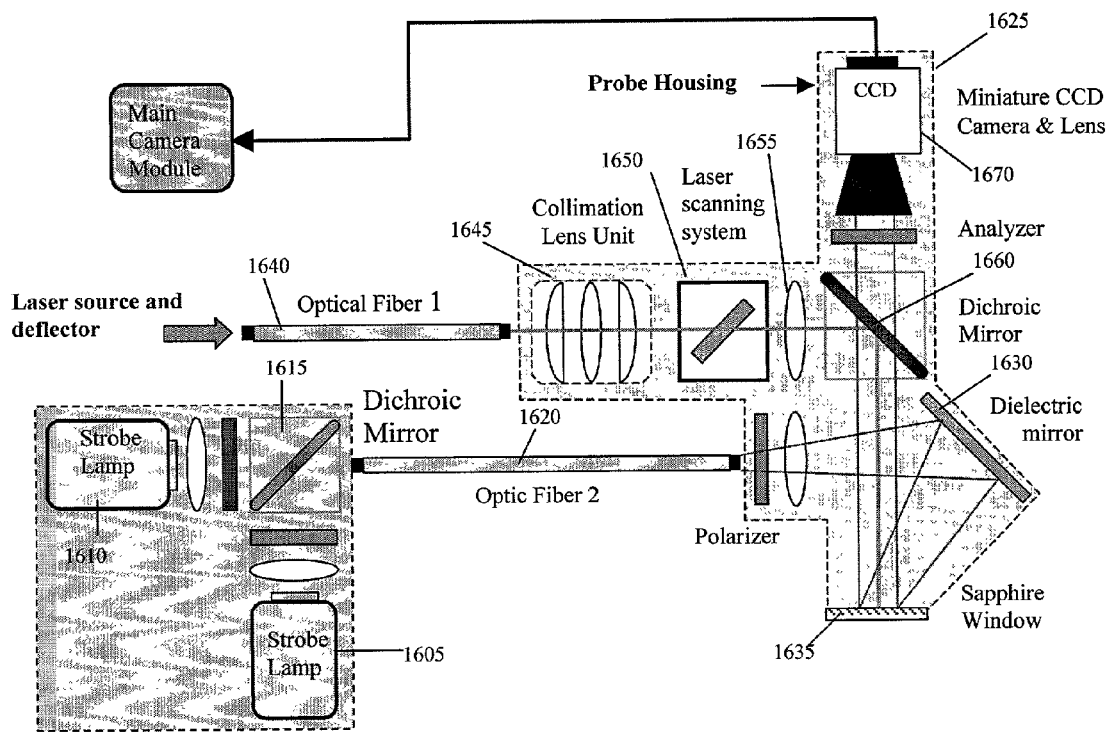
FIG. 16 a miniaturized Smart Scalpel system according to an embodiment of the invention.

FIG. 16 illustrates a miniaturized system 1600 according to an embodiment of the invention. Two strobe units 1605 and 1610 focus filtered light via a dichroic mirror 1615 onto an optical fiber 1620. Dichroic mirror has a cutoff wavelength at 600 nm (in between the 2 wavelengths) and may be used to prevent light loss. The light then passes through optical fiber 1620 to the probe 1625. This optical setup allows a single fiber (1620) to act as if it is two separate light sources. Inside probe 1625, light is reflected by a dielectric mirror 1630 onto sapphire window 1635. Since light from both channels illuminate from the same position, 2 images thus obtained may have the same intensity distribution and shadow details, and this allows image subtraction to be performed accurately.

A second optical fiber 1640 may bring a laser beam into probe 1625, where the beam passes through a collimation unit 1645, a 2-axis scanner 1650, a focusing lens 1655 and a dichroic mirror 1660. In order to keep the overall size small, a high resolution miniature camera is used. All other electronics and instruments that control system 1600 may be the same as system 100, as shown in FIG. 12.

Figure 17:
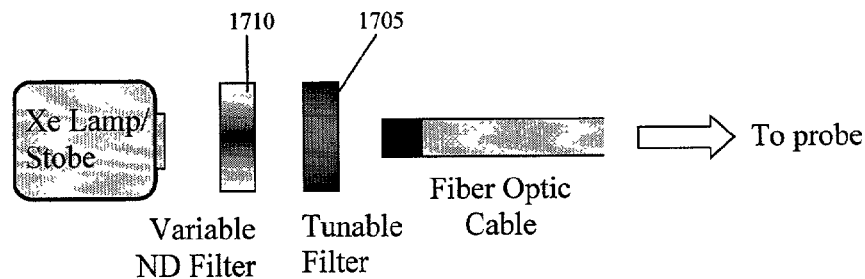
FIGS. 17 and 18 illustrate implementations of the system of FIG. 16 in accordance with the present invention.

Another design based on the same concept is shown in FIG. 17.

In this design, a liquid crystal tunable filter 1705 may be used to provide high frequency filtering between the 2 wavelengths. In order to match the light intensities at both wavelengths, a variable neutral density filter 1710 is placed before tunable filter 1705. Both these instruments may have high bandwidths and can be controlled digitally.

Figure 18:
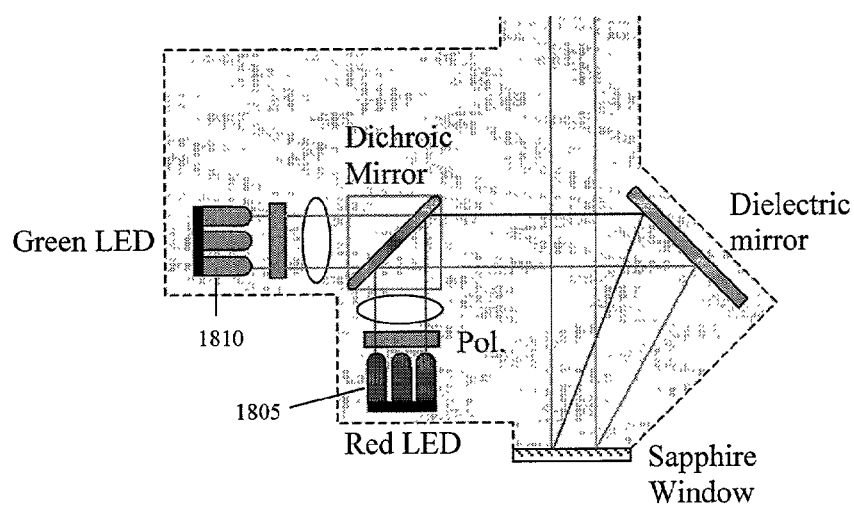

Another design may include illumination using light emitting diodes ("LEDs") 1805 and 1810, as shown in FIG. 18. InGaAlP LEDs are capable of producing a high amount of light output. As solid state devices, they are not subject to the maintenance requirements associated with lamp and shutter technologies, and are resistant to vibration and mechanical shock. Mostly importantly, the pulse width and brightness are easily controlled electronically. Lastly, LEDs are very small and cheap, and can be easily integrated into a probe.

It is noted that, however, strobe lamps can be digitally controlled very easily, and are able to produce a tremendous amount of light.

Detecting Blood Vessels in Images

In accordance with an exemplary embodiment of the invention, Smart Scalpel system 100 is used to treat PWSs. Accurate detection of blood vessels would improve effectiveness of such treatments. In order to detect blood vessels in images, a line extraction algorithm may be used. An important feature of the algorithm is that it should be fast in extracting the mid-line of the blood vessels so that the laser spot can heat the vessels accurately. Algorithms that may be used and detailed analysis of selected algorithms will now be described.

Lines may be characterized as ridges and valleys in an image. Without first stepping into the domains of ridge analysis, an initial approach for line detection may simply be binary thresholding to identify vessel regions, followed by skeletonization to extract essential lines. Due to the presence of noise and brightness variations, a raw image can be Gaussian filtered followed by contrast balance by subtracting with a median filtered image. The actual thresholding can be performed statistically, regionally, or by relaxation.

It was found that the above approach worked well only for clean images containing high contrast and well-defined blood vessels. However, this was not the case for images taken from the human skin. As a result, the thresholding produced inconsistent results, and the detection errors were too large. In addition, some of the regions identified did not exactly correspond to the blood vessels, which meant that the skeleton operation did not yield the actual vessel midline.

Line detection can be classified into three main categories. The first category detects lines by only considering gray values of an image. Line points are extracted by using purely local criteria, e.g., local gray value differences. Since this will generate a lot of false hypotheses for line points, elaborate and computationally expensive perceptual grouping schemes may need to be used to select salient lines in an image.

The second category is to regard lines as objects having parallel edges. In a first step, the local direction of a line is determined for each pixel, and then two edge detection filters are applied perpendicular to the line. Each edge detection filter is tuned to detect either the left or right edge of the line. The responses of each filter are combined in a non-linear way to yield the final response of the operator. The advantage of this approach is that since the edge detection filters are Gaussian derivatives, the procedure can be iterated over scale-space to detect lines of arbitrary widths. However, because special directional edge detection filters that are not separable may need to be constructed, the approach may be computationally expensive.

In the third category, the image is considered as a height map $z(x,y)$ and lines are extracted based on differential geometric properties. The basic idea behind these algorithms is to locate the positions of ridges and ravines in the image function. One such technique is to specifically identify the ridge edgels, which are locus of points where the image height is locally maximal in the transverse direction and the gradients are vanishing; this direction is equivalent to the minimum second directional derivative. Due to the high accuracy and computation efficiency, this method was selected for the Smart Scalpel application. Algorithms and methods to improve computation efficiency will now be described.

Figure 19A:
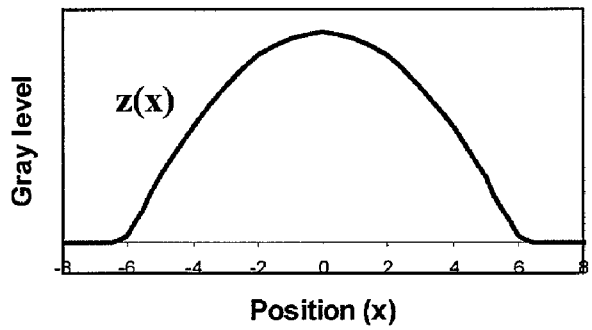
FIGS. 19A, 19B, and 19C are graphs showing a parabolic, a first derivative, and a second derivative profile, respectively.
Figure 19B:
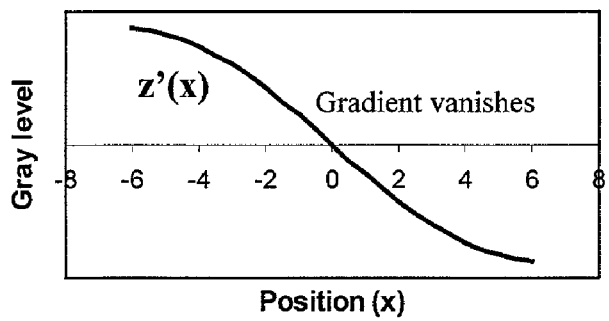
Figure 19C:
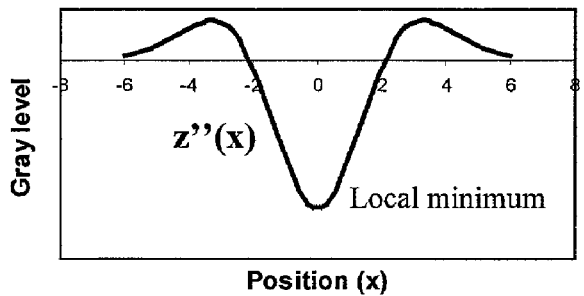

In order to detect lines in one dimension, say with a parabolic profile $z(x)$ shown in FIG. 19A, it may be sufficient to determine the points where first derivative $z'(x)$ vanishes. However, it is usually convenient to select only salient lines. A useful criterion for salient lines is the magnitude of second derivative $z''(x)$ at the point where $z'(x)=0$. In this case, a line point will have $z''(x) \ll 0$, as illustrated in FIG. 18C.

These properties can be easily extended to two dimensions. In this case, the center of the line is the position where the first directional derivative in the direction perpendicular to the line should vanish, and the second directional derivative should be of large negative value. These terms will be discussed in further detail below. It is also observed that the first derivative takes on its maximum absolute value at the edge of a line. Therefore, edges can be detected by locating the points where the first derivative is locally maximal in the direction of the gradient.

Since real images contain a significant amount of noise, it is not sufficient to estimate the first and second derivatives based only on the immediate neighbors. A better method to perform the estimates is by convolving (denoted by ⊗) the image with the derivatives of a Gaussian kernel:

$$\frac{\partial F(x, y)}{\partial x} = F(x, y) \otimes \frac{\partial G(x)}{\partial x}, \tag{6}$$

$$\frac{\partial^2 F(x, y)}{\partial x^2} = F(x, y) \otimes \frac{\partial^2 G(x)}{\partial x^2}, \tag{7}$$

$$\frac{\partial^2 F(x, y)}{\partial x \partial y} = F(x, y) \otimes \frac{\partial G(x)}{\partial x} \otimes \frac{\partial G(y)}{\partial y}, \tag{8}$$

where G is a one-dimensional Gaussian function and F(x,y) is the image. The Gaussian function and its derivatives are given by:

$$G_\sigma(x) = \frac{1}{\sqrt{2\pi}\,\sigma} e^{-\frac{x^2}{2\sigma^2}}, \tag{9}$$

$$\frac{\partial G(x)}{\partial x} = \frac{1}{\sqrt{2\pi}\,\sigma}\left(-\frac{x}{\sigma^2}\right) e^{-\frac{x^2}{2\sigma^2}}, \tag{10}$$

$$\frac{\partial^2 G(x)}{\partial x^2} = \frac{1}{\sqrt{2\pi}\,\sigma}\left(-\frac{x}{\sigma^2}\right)^2 e^{-\frac{x^2}{2\sigma^2}} - \frac{1}{\sqrt{2\pi}\,\sigma^3} e^{-\frac{x^2}{2\sigma^2}}, \tag{11}$$

where $\sigma$ is the standard deviation, also known as the resolution or scale-space parameter.

An image contains noise that may need to be removed prior to derivative estimations and line detection. Since noise is mostly high frequency signals, they can be suppressed using a two-dimensional low pass filter such as the Gaussian filter. This operation is also known as Gaussian smoothing. In two dimensions, the Gaussian function has a rotationally symmetric profile given by:

$$G_\sigma(x, y) = \frac{1}{2\pi\sigma^2} e^{-\frac{x^2+y^2}{2\sigma^2}}. \tag{12}$$

A two dimensional convolution is fairly simple to implement but is computationally expensive, especially for large width. However, a useful property of the Gaussian function is that a convolution with a two dimensional Gaussian can be separated into two orthogonal convolutions with one-dimensional Gaussians. This effectively reduces the number of operations per pixel from $N^2$ to 2N. Mathematically, this is equivalent to:

$$[\text{Image}] \otimes G_\sigma(x,y) = ([\text{Image}] \otimes G_\sigma(x)) \otimes G_\sigma(y), \tag{13}$$

where the one-dimensional Gaussian function $G_\sigma$ is given by Equation (9).

Due to this separable property, Gaussian convolutions are computationally efficient compared to convolutions based on other "low-pass" functions.

The scale-space parameter $\sigma$ (or resolution) is an important parameter due to the following reasons:

a. The choice of the resolution for smoothing creates a tradeoff between retaining the fine details of the line, which may correspond to high frequencies, and suppressing unwanted features due to noise. In general, larger values of $\sigma$ lead to better smoothing of the image but worse localization of the line.

b. The choice of $\sigma$ affects the width of the lines detected. A high resolution $\sigma$ extracts the major contours of an object, while the smaller resolutions extract finer image features. Unfortunately, when the resolution is scaled to fit the major contours, the finer contour details are often lost. Therefore, the value of $\sigma$ may be chosen carefully to extract blood vessels of a specified width.

c. A Gaussian kernel with large C has a large width and more coefficients. Hence, more mathematical operations may need to be performed during each convolution operation and this will slow down the image processing. (A method using recursive filters will be described later that will solve this problem.)

d. The choice of $\sigma$ affects the maximum negative response of the second directional derivative in scale-space. The higher the resolution $\sigma$, the smaller the second derivative will be. Hence, the threshold to select salient lines may need to be set to an accordingly smaller value. These concepts will become clear when they are discussed in the later sections.

Some of the problems described above can be solved by detection at multiple scales of resolution (or detection at repeated convolutions using small resolutions). However, this method is computationally expensive and is not practical in a time-critical application.

Two methods of implementing the Gaussian convolution are used.

The direct convolution produces an output sequence y(i) that is the weighted sum of the current and past inputs x(i), where $h_k$ is the coefficients of the convolution kernel of width N:

$$y(i) = \sum_{k=0}^{N-1} h_k x(i-k). \tag{14}$$

This operator is also known as a Finite Impulse Response (FIR) filter because the impulse response has finite width, i.e. it is non-zero only over a finite interval. FIR suffers from the fact that it is computationally expensive since the width of the kernel N is generally large, and the number of operations per point is proportional to the number of coefficients.

An Infinite Impulse Response (IIR) filter produces an output y(i) that is the weighted sum of the current and past inputs x(i) and past outputs y(i−k). The IIR has an impulse response of infinite width and is implemented recursively. This filtering technique deals with the determination of the coefficients $a_k$'s and $b_k$'s of the following recursive system of order n:

$$y(i) = \sum_{k=0}^{m-1} b_k x(i-k) - \sum_{k=1}^{n} a_k y(i-k), \tag{15}$$

so that the transfer function best approximates, in a least-square criterion, that of the non-recursive FIR system.

The key to the approach of the IIR is the derivation of an exponentially based filter family that well approximate the Gaussian filters of the same resolution ($\sigma$), and then to implement the filters in a recursive way. The methods will be discussed in further detail below.

Dealing with the causal recursive system given by Equation (15) instead of the non-recursive system (14) reduces the number of operations per output element from N to m+n (where m+n<N). In addition, recursive filtering is done with a fixed number of operations per point independent of the resolution (σ) of the Gaussian function. Therefore, it is computationally efficient and requires much fewer computational steps than direct or frequency domain convolution using the Fast Fourier Transform.

The disadvantage of the IIR is that the results are less accurate than a FIR. This error can be reduced by using a higher order filter that contains more coefficients but is slower. In addition, the result becomes less accurate when the image size is very small. This is because recursive filtering depends on the previous outputs and a very small sample may not allow it to accumulate enough information to compute the current output.

A discrete theory was proposed that the scale-space properties in the continuous case transfer directly to the discrete domain, and operators that commute before discretization also commute after discretization. One important computational implication of this is that image derivatives can be computed directly from smoothed data, and that will give the same result as convolution with the corresponding derivative kernel.

For example, if 5 different derivatives are to be approximated, there is no need to separately convolve the image with 5 large support derivative kernels. The same result can be obtained by smoothing the image with a large support Gaussian kernel, followed by computing the derivatives using 5 small support difference operators. On hindsight, this means that there is no need for re-doing the smoothing part of the transformation for 4 extra times. The difference operators for computing the derivatives (after smoothing) are given by:

$$\frac{\partial F(x, y)}{\partial x} \approx \frac{1}{2\epsilon}[F(x+1, y) - F(x-1, y)], \quad (16)$$

$$\frac{\partial F(x, y)}{\partial y} \approx \frac{1}{2\epsilon}[F(x, y+1) - F(x, y-1)], \quad (17)$$

$$\frac{\partial^2 F(x, y)}{\partial x^2} \approx \frac{1}{\epsilon^2}[F(x-1, y) - 2*F(x, y) + F(x+1, y)], \quad (18)$$

$$\frac{\partial^2 F(x, y)}{\partial y^2} \approx \frac{1}{\epsilon^2}[F(x, y-1) - 2*F(x, y) + F(x, y+1)], \quad (19)$$

$$\frac{\partial^2 F(x, y)}{\partial x \partial y} \approx \frac{1}{4\epsilon^2}[F(x+1, y+1) + \\ F(x-1, y-1) - F(x+1, y-1) - F(x-1, y+1)] \quad (20)$$

From all the methods proposed in this section, it can be deduced that the most efficient way of computing the derivatives is to smooth the image using IIR filters in a separable manner, following by derivative approximation using the small support difference equations.

Ridge edgel detection involves finding local extrema in special directions. Therefore, we need to introduce the concept of directional derivatives, which measures how functions vary when restricted to a subset of its domain. As mentioned above, the zeros of first directional derivatives in the direction perpendicular to the ridge lines are candidate edgel points. This perpendicular direction corresponds to the direction of largest principle curvature, which is also the direction of minimum second directional derivative. In the case of a ridge, this derivative has a large negative value compared to its orthogonal principal curvature, which has magnitude close to zero.

Let $\vec{n}$ be a vector pointing in the direction of largest principle curvature. Given an image function F, the first directional derivative in the direction $\vec{n}$ is defined by:

$$(\vec{n} \cdot \nabla) F(x, y) = \sum_{i=1}^{2} \vec{n}_i \frac{\partial F(x, y)}{\partial x_i}. \quad (21)$$

Similarly, the second directional derivative in the direction $\vec{n}$ is defined by:

$$(\vec{n} \cdot \nabla)^2 F(x, y) = \sum_{i=1}^{2} \sum_{j=1}^{2} \vec{n}_i \frac{\partial^2 F(x, y)}{\partial x_i \partial y_j} \vec{n}_j = \vec{n}^T Hess(F) \vec{n}, \quad (22)$$

where Hess(F) is the Hessian matrix given by:

$$Hess(F) = \begin{bmatrix} \frac{\partial}{\partial x^2} F(x, y) & \frac{\partial}{\partial x \partial y} F(x, y) \\ \frac{\partial}{\partial x \partial y} F(x, y) & \frac{\partial}{\partial y^2} F(x, y) \end{bmatrix}. \quad (23)$$

The vector $\vec{n}$ and the magnitude of the second directional derivative can be computed from the eigenvectors and eigenvalues (K) of the Hessian matrix. In the case of a ridge, the eigenvector that corresponds to the minimum eigenvalue ($K_{min}$) is in the direction of the largest principle curvature.

With the directional derivatives thus defined, the image F(x,y) has a local maxima if the following conditions are true:

$|K_{mm}| >> |K_{max}|$ and Hess(F) is negative definite.

$(\vec{n} \cdot \nabla) F(x,y) = 0$

An algorithm for implementing the ridge detection technique mentioned above will now be described in detail.

To determine the location of a line, one could use a zero crossing detector to find points where the first directional derivative vanishes. However, this would yield the position of the line only with pixel accuracy. In order to overcome this, this algorithm proposes to detect the lines by locally approximating the image function F(x,y) by its second order Taylor polynomial. The coefficients of the polynomial are determined by convolving the image with the derivatives of a Gaussian kernel. This polynomial is given by:

$$F(x,y) = R + (R_x x + R_y y) + \frac{1}{2}(R_{xx} x^2 + 2R_{xy} xy + R_{yy} y^2), \quad (24)$$

where $R_x$, $R_y$, $R_{xx}$, $R_{xy}$ and $R_{yy}$ are the locally estimated derivatives at (x,y).

Curvilinear structures in 2D can be modeled as curves s(t) that exhibit a characteristic 1D line profile in the direction n(t) perpendicular to the line. Based on ridge analysis, the direction in which the second directional derivative s"(t) takes on its maximum absolute value will be used as the direction n(t). This direction can be determined by calculating the eigenvalues and eigenvectors of the Hessian matrix (which is negative definite at a line point):

$$H(x, y) = \begin{pmatrix} r_{xx} & r_{xy} \\ r_{xy} & r_{yy} \end{pmatrix}. \quad (25)$$

The calculation can be done in a numerically stable and efficient way by using one Jacobi rotation to annihilate the $r_{xy}$ term. The eigenvector that points in the direction n(t) is then given by the eigenvector that corresponds to the maximum absolute eigenvalue. Now, let this eigenvector be given by $(n_x,n_y)$ with $\|(n_x,n_y)\|=1$. A quadratic polynomial is then used to determine whether the first directional derivative along $(n_x,n_y)$ vanishes within the current pixel. This zero-crossing point is given by:

$$(p_x,p_y)=(tn_x,tn_y), \quad (26)$$

where $$t = -\frac{R_x \hat{n}_x + R_y \hat{n}_y}{R_{xx}\hat{n}_x^2 + 2R_{xy}\hat{n}_x\hat{n}_y + R_{yy}\hat{n}_y^2}. \quad (27)$$

The point is declared a line point if this position falls within the pixel's boundaries, i.e. $(p_x,p_y) \in [-\frac{1}{2}, \frac{1}{2}] \times [-\frac{1}{2}, \frac{1}{2}]$. The magnitude of the second directional derivative can be used to select salient lines. The mathematical theories and proofs for the above equations will be discussed in further detail below.

Pixels that are marked as line points have different magnitudes (or strengths) of the second derivative along $(n_x, n_y)$. Line points with high saliency have higher strengths. Rather than simply selecting a global threshold value to extract the salient line, which is highly inaccurate, a thresholding technique using hysteresis is used. (Note that an 8-bit dynamic range expansion can be performed prior to thresholding.)

Hysteresis thresholding uses a high threshold $T_H$ and a low threshold $T_L$. Any pixel in the image that has a value greater than $T_H$ is presumed to be a line pixel, and is marked as such immediately. Then, any pixels that are connected to this line pixel and that have a value greater than $T_L$ are also marked as line pixels. For example, if a line pixel is assigned as white (pixel value 255) and non-line pixel as black (pixel value 0), then this algorithm is given mathematically as:

$$Result(x, y) = \quad (28)$$
$$\begin{cases} Pixel(x, y) > T_H & \rightarrow Result(x, y) = 255 \\ Pixel(x, y) > T_L \text{ and } Pixel(neighor) > T_H & \rightarrow Result(x, y) = 255 \\ Pixel(x, y) > T_L \text{ and } Pixel(neighbor) < T_H & \rightarrow Result(x, y) = 0 \\ Pixel(x, y) < T_L & \rightarrow Result(x, y) = 0 \end{cases}$$

The marking of neighbors is performed recursively for computational efficiency.

The results are shown in FIGS. 20A, 20B, and 20C. The resolution ($\sigma$) used was 3.0, and hysteresis thresholding was carried out at $T_H=35$ and $T_L=21$.

There are numerous line detection methods that use similar concept. Some methods even extend the derivative analysis up to $3^{rd}$ orders. In general, the robustness and computational efficient of these methods vary, depending on what the application is for. In the detection of blood vessels from skin images, it is found that the polynomial approximation technique gives excellent results at a relatively high speed.

A line is bounded by an edge on each side. To detect the width of each line point, the edge pixels to the left and right can be searched for exclusively along a line in the direction perpendicular to the line.

The Canny edge detector has been identified as a suitable algorithm. The first reason is that this detector has been widely recognized as a standard technique due to its accuracy. The second reason is that Canny edge detector uses the Gaussian first derivatives, which are in fact computed as a "by-product" during line detection. Therefore, the computationally expensive convolutions can be skipped and the rest of the detection process becomes trivial.

The algorithm consists of three stages: gradient & direction computation, non-maximum suppression and hysteresis thresholding.

As mentioned before, the first derivative takes on its maximum absolute value at the edge of the line. Therefore, edges can be detected by locating the points where this gradient magnitude is locally maximal in the direction of the gradient. The gradient magnitude at a pixel (x,y) is defined as:

$$G(x, y) = \sqrt{\left(\frac{\partial F(x, y)}{\partial x}\right)^2 + \left(\frac{\partial F(x, y)}{\partial y}\right)^2}. \quad (29)$$

There is no need to compute these partial derivatives since they were already computed during the line detection process. To speed up computation, this gradient magnitude can also be approximated as the sum of the absolute values of the partial derivatives.

The direction of the gradient at each pixel (x,y) can be estimated as:

$$\theta(x, y) = \tan^{-1}\left(\frac{\frac{\partial F(x, y)}{\partial y}}{\frac{\partial F(x, y)}{\partial x}}\right). \quad (30)$$

In non-maximum suppression (NMS), the edges are thresholded based on the direction of the gradient at each pixel. The basic principle is that the magnitude of the gradient at an edge pixel should be greater than that of its neighbors that lie on opposite sides and along the same gradient direction.

Figure 21:
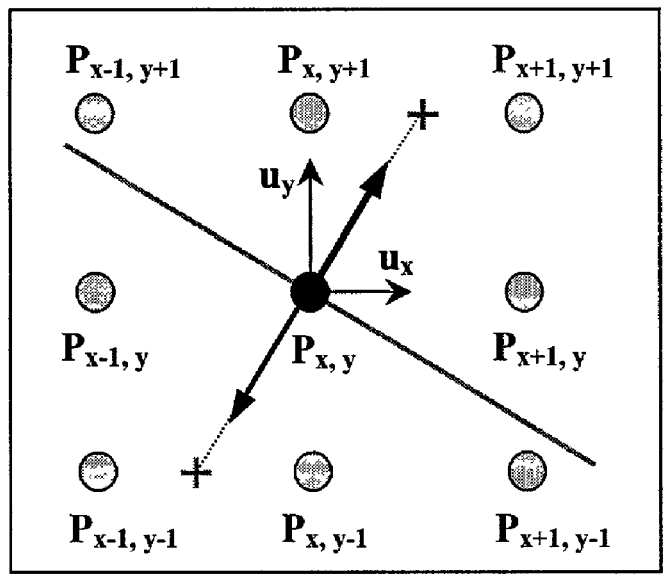
FIG. 21 is a diagram for illustrating the non-maximum suppression principle used in accordance with an embodiment of the invention.

The algorithm uses a nine-pixel neighborhood centered on pixel $P_{x,y}$, as shown in FIG. 21. The normal to the edge direction is shown as an arrow, and has components $(u_x, u_y)$. This is the direction that non-maximum suppress on the gradient magnitude needs to be implemented. In general, this direction does not point directly to any pixels $P_{ij}$, where the gradient magnitude is known. Therefore, it is necessary to estimate the gradient magnitude at a point between the two pixels which lie closest to the line through $P_{x,y}$ in the direction u. Two of these points are marked as "+" in FIG. 21.

If it is assumed that the gradient changes linearly as a function of position, then the gradient magnitude can be interpolated using the vector u. In FIG. 21, the gradient must be interpolated from the two points given by $P_{x,y+1}$ and $P_{x+1,y+1}$. The value of this interpolated gradient is then given by:

$$G_1 = \frac{u_x}{u_y} G(x+1, y+1) + \frac{u_y - u_x}{u_y} G(x, y+1), \quad (31)$$

where G(i,j) is calculated from Equation (29). Similarly, the interpolated gradient at a point on the opposite side is:

$$G_2 = \frac{u_x}{u_y} G(x-1, y-1) + \frac{u_y - u_x}{u_y} G(x, y-1). \quad (32)$$

The point $P_{x,y}$ is marked as an edge if $G(x,y) > G_1$ and $G(x,y) > G_2$. In general, there are eight major cases to check for, and some shortcuts can be made for efficiency's sake.

As in line detection, hysteresis thresholding is implemented to extract the salient edges more accurately. This may be done by immediately accepting edge points that have a gradient magnitude larger than $T_H$ and rejecting points that have a gradient magnitude smaller than $T_L$. All other edge points are accepted if they are connected to accepted points by a connected path.

The pulse width of the laser depends on the thermal relaxation time of the blood vessels, which in turn depends on the vessel diameter. Therefore, it is desirable to compute the width of the blood vessel in the image so that the laser parameter can be adjusted during treatment.

One algorithm to detect line width made use of the fact that the scale-space parameter σ of the Gaussian influences the scale-normalized response of a line as a function of line width. This algorithm can be performed by iteration through scale-space while selecting the scale that yields the maximum response of the desired line width. However, the high amount of convolutions makes this computation extremely expensive, especially if one is only interested in lines in a certain range of widths. Furthermore, this approach would only yield a coarse estimate of the line width, since the scale-space is quantized in rather coarse intervals.

A line is bounded by an edge on each side. Therefore, one method to compute the width of each line point is to search for the edge pixels to the left and right in the direction n(t) perpendicular to the line. As mentioned earlier, if the Canny edge detector is used, there is no need to perform any expensive convolutions operations. In addition, the normal n(t) need not be computed since it was already computed once during line detection. Hence, this technique not only estimates the line width accurately, but also performs the computation efficiently.

Once the edges are located, then moving in the positive n(t) direction until an edge pixel is found will yield half the width, and performing the same operation in the reverse direction will yield the other half. The width of the line is then given by the sum of the 2 half widths.

All image acquisition processes are subject to noise of some type. There are two types of noise that are of specific interest in image analysis. Signal-independent noise is a random set of gray levels that is statistically independent of the image data. They are added to the pixels in the image to give the resulting noisy image. This kind of noise occurs when an image is transmitted electronically from one place to another. If A is a perfect image and N is the noise that occurs during transmission, then the final image B is:

$$B = A + N. \quad (33)$$

A and N are unrelated to each other. The noise image N could have any statistical properties, but a common assumption is that it follows the normal distribution (central-limit theorem) with a mean of zero and some measured or presumed standard deviation. This type of noise is referred to as a Gaussian noise.

The second major type of noise is called signal-dependent noise. In this case, the level of the noise value at each point in the image is a function of the gray level there. The grain seen in some photographs is an example of this sort of noise, and it is generally harder to deal with. Fortunately, it is of less importance, and becomes manageable if the image is sampled properly.

Noise can be artificially added to an image. Deliberately corrupting an image with noise allows us to test the resistance of an image processing operator to noise and assess the performance of various noise filters. The additive noise should be evenly distributed over the frequency domain (white noise). Since noise is dominantly high frequency signal, they can be suppressed using low pass filters such as Gaussian or median filters.

To produce a noisy image B from an original image A, Gaussian noise with a mean $\mu_n$ and a variance $\sigma_n^2$ can be added by:

$$B = A + (\sigma_n * Rand) + \mu_n, \quad (34)$$

where Rand is a normally distributed random number. This task can be performed in Matlab under the function "imnoise( )". The signal-to-noise (SNR) of an image is also defined as:

$$SNR = \sqrt{\frac{\sigma_A^2}{\sigma_n^2} - 1}, \quad (35)$$

where $\sigma_A^2$ is the variance of the original image A.

Figure 22:
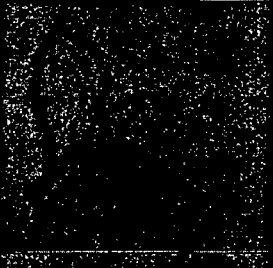
FIG. 22 demonstrate results of image processing performed in accordance with an embodiment of the invention.

Noise was added to an original image to test the effectiveness of the line detection algorithm. The results are shown in FIG. 22.

It can be seen that the algorithm performed well in the presence of noise. By increasing the resolution (σ) of the Gaussian operator, the noise can be further suppressed before the line detection begins. However, this is done at the expense of losing useful and fine image details.

It is also observed that changing the image contrast has almost no effect on the accuracy of the algorithm. Most of the lines that are nearly visible to the eyes are still being detected. Therefore, noise is identified as the dominant factor for most detection errors.

The speed of the algorithm was tested on the earlier image. The image size is 400 by 400 pixels and the test was performed on a Celeron 466 MHz computer. The method used to compute the derivatives are the discrete approximations discussed above regarding equations (16)–(20). The processing times are summarized in FIG. 23.

Thus, in accordance with an exemplary embodiment of the present invention, a method to extract curvilinear structures is used. The approach is based on the differential geometric properties of an image function. For each pixel, the second order Taylor polynomial is computed by convolving the image with Gaussian filters. Line points are required to have a vanishing gradient and a high curvature in the direction perpendicular to the line. In order to achieve high computation speed, the derivatives are estimated using IIR Gaussian filters and small support difference operators.

Imaging Strategy

The expensive computation associated with convolution operations limits the bandwidth of the system. This problem can be solved in 3 ways: software, hardware and strategy. As shown above, the software solution is the use of IIR filters for convolution. The hardware solution is simply the use of faster processor and instruments. A third solution, which is the design of a suitable imaging strategy to meet a bandwidth requirement, will now be described.

To operate at a bandwidth of 6 Hz, the time required for each feedback loop is 167 ms. If the dwell time of the laser on each target is 5 ms, the laser can only treat 34 targets in an image field which contains potentially up to 18271 targets (using a camera resolution of 755×484 pixels and assuming the blood vessels cover 5% of the image field). This is equivalent to treating only 0.2% of the blood vessels in 1 operation loop, and without taking into account the time taken for grabbing the images and processing them. In another words, it is impossible for the laser scalpel to treat the entire region in 1 operation loop. Therefore, the region may need to be divided into many smaller regions, where the treatment for each small region will be carried out within 167 ms.

The bandwidth of the system is governed by the following equation:

$$\text{Bandwidth} = \frac{1}{T_{grab} + T_{galvo} + T_{system} + T_{laser} + T_{proc}}, \quad (36)$$

where:
1. $T_{grab}$ is the time taken by the program to grab an image. It depends on both the speed of the camera and the frame grabber, and is currently 66.7 ms per grab. 2 grab operations from the green and red channels are required per operation loop, and this adds up to 133 ms;
2. $T_{galvo}$ is the step response of the scanning galvanometers, which have settling times on the order of 10 ms;
3. $T_{system}$ is the delay due to hardware systems such as the data acquisition board;
4. $T_{laser}$ is the time required for the laser to thermally treat N blood vessel targets. This value is fixed by the treatment specifications, and the laser pulse width is typically 1 to 10 ms per target;
5. $T_{proc}$ is the time taken for image processing. It depends on the processing speeds of both the computer and the image analysis algorithm, and constitutes the main bottleneck in the feedback loop due to the high amount of computations required.

Based on the current instruments, the only area that can be improved is $T_{proc}$, which is also the bottleneck in the feedback loop. In addition, the times taken up by $T_{grab}$, $T_{galvo}$ and $T_{system}$ only allow a window of less than 34 ms for image processing and laser treatment. Therefore, dividing the image field into smaller regions to process is a good way to speed up the process loop.

A simple division of the image field into equal squares or rectangles is not good enough to deal with the speed problem. This situation can be described in the view of FIG. 24A.

FIG. 24A shows an image field divided into 6 equal regions. Region 4 contains more targets than the other regions while region 6 contains no target at all. This scenario will present the following problems:

1. Convolution and other image processing operations will be wasted on region 6, which contains no target at all.
2. Image processing need not be performed on the entire regions 1 and 5, which contains very few targets.
3. The processing time for regions with more targets (e.g. region 4) will be longer than those with fewer targets. Thus, the processing times of each regions will be unequal.
4. Regions with more targets are laser treated for longer times.

Therefore, it is clearly shown that equal division will lead to both time wasting and non-uniform operation times for each region. In this case, the blood vessels cannot be consistently tracked. On the other hand, the image field can be divided into much smaller regions so that the inconsistencies can be scaled down. However, these regions may need to be so small that there will be too many of them to make the whole operation efficient and practical.

A better approach would be to divide the image field into regions that contain an equal number of targets. Parts of the image that contain no target will be ignored. This will solve all the problems encountered in the previous approach. However, in order to do this, the locations of the targets may need to be estimated beforehand. This means that the tissue may be scanned once to determine the approximate target locations before the actual treatment with feedback can take place. This method will take a longer treatment time but it guarantees that the feedback bandwidth will be fast.

The steps to implement the regional division scheme discussed above will now be described.

Step 1: First Pass Imaging

As shown in FIGS. 24B and 24C, this involves grabbing a red and green image to perform background subtraction and image analysis to identify the blood vessels. The locations of the blood vessels are marked as S(x,y), which are referred to as the seed pixels. This first pass imaging will take approximately a few seconds.

Step 2: Grow Area from Seed Pixels

Since the patient may move after the first pass imaging, the subsequent positions of the blood vessels may not be in the same position S(x,y). However, these new positions will be very near its original positions if the patient is sufficiently still, or if the Smart Scalpel is held securely to the skin. Therefore, an area can be "grown" around the seed pixels, which will represent future vessel positions. These possible targets will be called T(x,y).

Figure 24D:
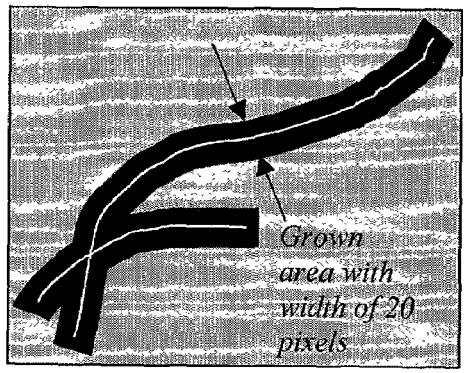

In order to determine how much area is to be "grown", we need to estimate how much the patient may move. As mentioned before, the tremor displacement is approximately 370 µm. Now, assuming that 370 µm represents 10 pixels in the image (actual value may be calibrated using reticles), then an area 20 pixels wide may be grown around the seed pixels, as shown in FIG. 24D.

From this point onwards, all subsequent image processing operations will only be performed on T(x,y). This will ensure that no operation is wasted on parts of the region that contains no target. For example, if the blue region covers 20% of the image, then the subsequent image processes on the whole image will be 5 times faster.

Step 3: Regional Division

Figure 24E:
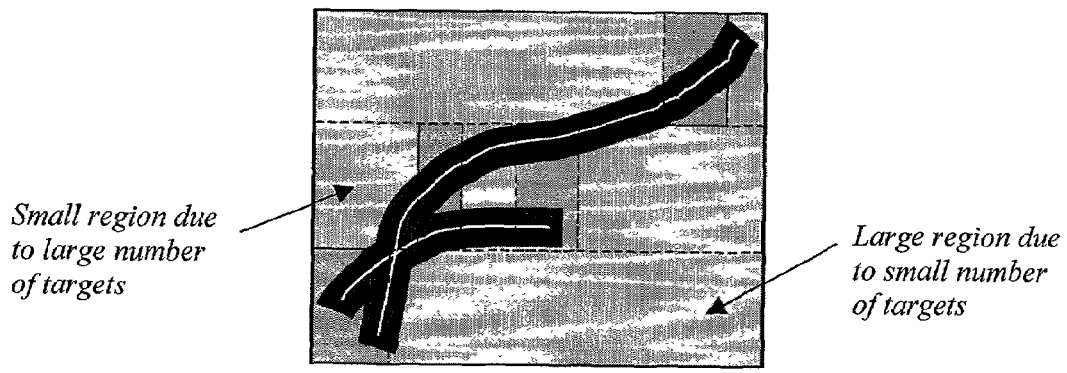

The image field will now be divided into rectangular regions that contain the same number of seed pixels S(x,y). The image is first divided into several equal rows, and then the program pointer will count the number of seed pixels within each row (from left to right) and define a boundary when a specified number N is reached. In this way, rectangular regions of equal height but unequal width will be defined, as illustrated in FIG. 24E, where each region contains the same N number of targets.

In order to deal with the case where the blood vessels in one region may move to its neighboring region during treatment, the regions are made to overlap each other by a certain number of pixels. However, since the region width can be very narrow in a highly congested area, the number of pixels overlap is chosen to be 2.

With the regions now defined, the final step is the feedback operation, where the operation loops are sequentially performed on each region.

The time taken by one operation loop depends on the size of the region it process, which is determined by the number of "seed" targets N. In general, a large value of N will lead to big regions and low bandwidth, while a small value of N will create a large number of regions which will slow down the overall process.

The strategy proposed above is used to meet a bandwidth requirement. However, if faster computer and instruments are utilized so that speed is no longer restricted, then the imaging strategy may be changed. Laser treatment may be performed immediately without having to implement a first pass scan because the image processing is able to handle a much larger area. In this case, a dynamic region approach may be used:

1. At the start of the treatment, a reasonably large region is defined at one corner of the image. Image analysis and laser treatment will only be performed inside this region.
2. At the first treatment loop, once N number of targets have been detected in the region, the image analysis will terminate and the laser treatment will begin. The value of N is chosen to meet the bandwidth requirement.
3. After the N targets have been treated, the region will now be dynamically shifted to cover the nearest area that has not been processed. Then, the image analysis and laser treatment on N newly detected targets will begin on the new position.
4. This region will shift systematically until the entire image has been covered.

As before, the purpose of defining a region is for computation efficiency, and the purpose of treating a fixed N number of targets is to achieve uniform operation times per treatment loop.

Besides region strategies, another idea was two-point tagging of the imaging object. If the object was tagged with two markers within the field of view, then they serve as fiducial points and any translation and rotation of the object can be calculated from the relative movement of the line formed. Therefore, if the shape of the blood vessels with respect to the markers is determined before the feedback-treatment begins, then the time-consuming line detection algorithm may not need to be performed. The only image analysis required is to determine the positions of the markers by finding their centers of mass (Com). This algorithm can be easily performed by thresholding to isolate the markers, followed by a Com finder or morphological skeletonization. Matrix algebra can then be performed to determine the translation and rotation.

This method assumes that the shape of the object is preserved, which is reasonable if the patient is held sufficient still so that the tissue is not stretched or compressed during treatment. Since the field of view is only 17 mm by 13 mm, the markers must be small and placed at very short distances apart. Therefore, this poses the problem of placing these markers over an extensive area of the skin. However, if the lesion area is small enough, then this technique becomes feasible. Another idea was to look for tags within the image itself, such as the end of vessels and junctions. However, this becomes a problem if the blood vessel pattern is too complicated.

The treatment is more effective if the laser pulse width is based on the thermal relaxation time of the blood vessels. Larger diameter vessels have longer thermal relaxation times and consequently require longer laser pulse widths. Based on the image algorithm discussed, the diameter of the blood vessels can be approximated by determining the distance between the edges on opposite sides of the line. If this algorithm is implemented during the feedback operation, it will reduce the bandwidth due to the extra computations required.

If the system bandwidth is not to be affected, one solution is to perform the width detection during the first pass imaging stage (Section 0), and "grow" different types of regions that correspond to a specified range of widths. The algorithm is described as follows:

1. Assign the width of lines into several groups, where each group has its specified range, e.g. from 10 μm to 30 μm.
2. Perform the first pass image processes to determine the lines and their widths.
3. Group the line pixels according to their width, and "grow" different types of regions around them depending on their group. This step is exactly the same as Section 0 except that the regions grown are tagged to represent different widths.
4. During the feedback operation, there is no need to compute the width anymore; the laser pulse width is adjusted depending on the type of region that the blood vessel is in. In this way, there is no change to the treatment bandwidth.

This algorithm assumes that blood vessels of a particular width stay within their assigned regions during treatment. This assumption is reasonable since the width of blood vessels changes gradually, except at distributary junctions. This algorithm will become problematic if the widths differ by too much or too frequent along a line because it becomes difficult to generate the regions.

Figure 25A:
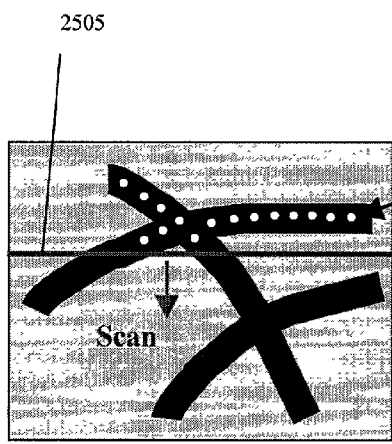
FIGS. 25A and 25B illustrate scanning schemes for laser treatment according to an embodiment of the present invention.

There are two strategies for laser treatment, raster scan and line tracing. Raster scan involves a row-by-row scanning of the regions, and the beam shutter is opened when the scan is directly above the blood vessels. This technique is illustrated in FIG. 25A where horizontal line 2505 represents the computer program searching for targets from top-down, and the white circles represent the targets. The scan is implemented after all the blood vessel coordinates within the region are determined. In addition, since it may not be necessary to apply laser onto every pixels, the treatment process can be speeded up if the laser scan is skipped every few rows and columns.

Figure 25B:
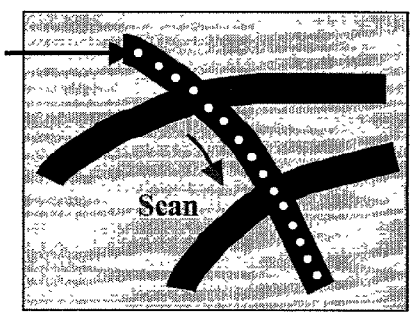

Unlike raster scan, which is "random", line tracing involves tracing the laser beam along blood vessels (FIG. 25B). The tracing along a particular blood vessel will be continuous as long as the imaging algorithm detects it as a continuous line. Although the line tracing algorithm appears to be more complicated, it does not lose computational efficient to the raster scan because it can be easily incorporated into the hysteresis thresholding algorithm described above. This means that the image processing program will locate the line pixels and execute the laser scan simultaneously. In terms of the laser treatment, this scheme is better than the raster scan because the laser will heat along a single blood vessel continuously, thus ensuring that the blood vessel is exposed to the thermal energy for a longer period of time.

In terms of speed, both strategies may outdo each other depending on the distribution of blood vessels. The distribution that allows the galvanometers to rotate a less overall angle will complete the scan faster. However, the raster scan may have a slight edge over the line tracing because the galvanometers used are tuned for raster scans.

Clinical Human & Animal Imaging

Before the Smart Scalpel is used to treat human patients, imaging are carried out on humans and animals to test the both the optical system and the image analysis algorithms. This library of images can also help to determine the type of vascular lesions the Smart Scalpel is most suited to treat.

To reduce specular reflection, 3 types of index matching gel were tested. They were (1) Aquasonic™ Transmission Gel (Parker Laboratories), (2) Vidal Sassoon™ styling gel, which is particular effective for confocal tissue imaging and (3) Johnson's™ Baby Oil Gel.

It was found that the Johnson's™ Baby Oil Gel was the most suitable. This gel is colorless and is the least viscous. During tissue imaging, it was found that the level of viscosity allows the gel to spread easily and therefore, any air pockets formed were easy to remove. A spectral analysis indicated that the absorption is almost negligible and the profile is flat.

To assess the imaging performance of the Smart Scalpel and the image processing algorithms, images of a rabbit's ear were taken with the system. The rabbit was a New Zealand rabbit, and hair was removed from the ear before the images were taken.

There was little amount of pigments in the ear, and the blood vessels were clearly visible with the naked eye. They appear red against the milky-white tissue background. The blood vessel structure consisted of a central artery running along the middle of the ear, and tiny vessel distributaries spreading from it. The small blood vessels were typically found near the end and at the edge of the ear. The central artery was approximately 2 mm while the smallest blood vessel was approximately 80 µm.

Figure 26A:
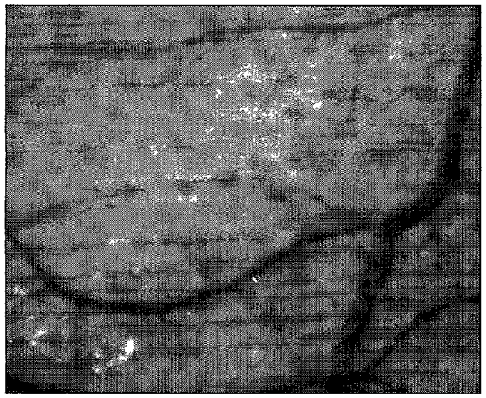
FIGS. 26A and 26B illustrate results of the image processing according to an embodiment of the invention on an animal scan.

An image taken from the end of the ear is shown in FIG. 26A.

The blood vessels were clearly visible from the image taken, and the contrast against the background was excellent. The largest vessel on the right was approximately 470 µm, while the medium vessel at the low part of the image was approximately 250 µm. The very fine vessels were approximately 100 µm.

Figure 26B:
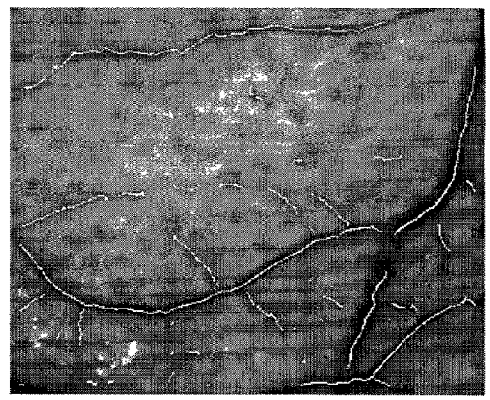

The image processing algorithm was successful in detecting most of the blood vessels. The result of the previous image is shown in FIG. 26B.

Figure 27A:
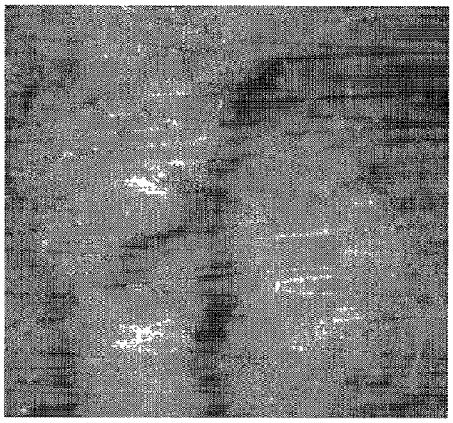
FIGS. 27A and 27B illustrate results of the image processing according to an embodiment of the invention on a human scan.
Figure 27B:
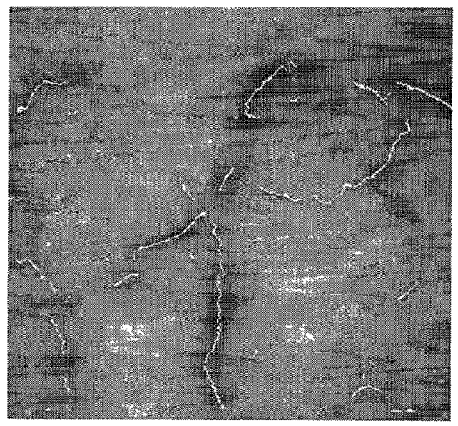

Images taken from human patients also have successful results. The ORS-OPS imaging techniques employed was able to produce high contrast images of the blood vessels that would not be possible with other imaging methods. The image shown in FIG. 27A was taken from ecstatic leg vein at the foot. The blood vessel was clearly visible against the background. The size of the central large vessel was approximately 450 µm. The image processing result is shown in FIG. 27B whereby the algorithm was successful in detecting most of the blood vessels.

Laser Treatment on Animals

To test the Smart Scalpel's close-loop treatment method, laser treatments are performed on a rabbit's ear. The rabbit is anesthetized and hair is removed from its ear before the treatment. The laser parameters used are as illustrated in FIG. 28.

Figure 29A:
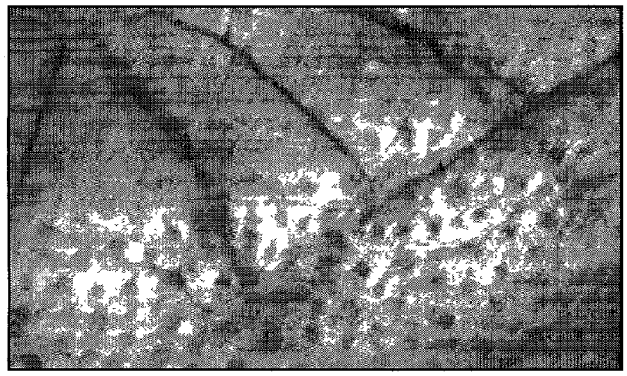
FIGS. 29A, 29B, 29C, 30, and 31 illustrate results of treatment effected according to an embodiment of the invention.
Figure 29B:
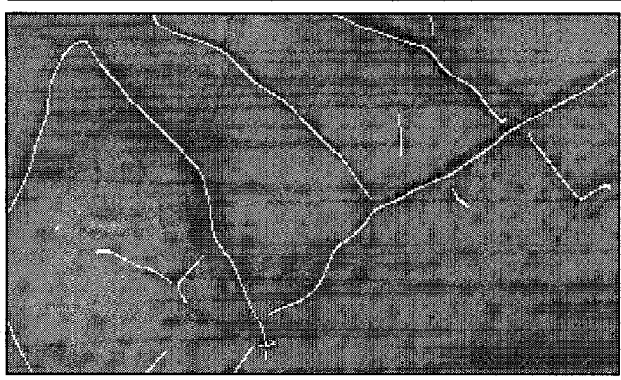
Figure 29C:
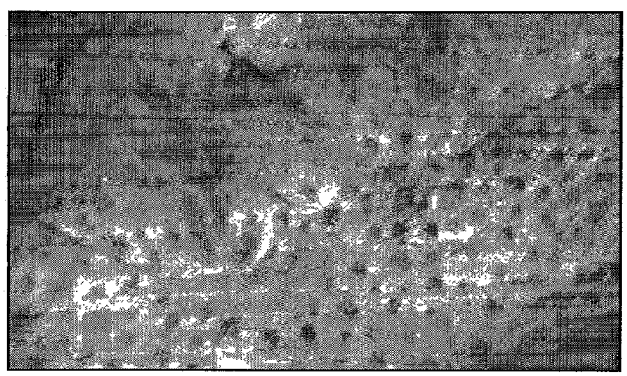

FIGS. 29A, 29B, and 29C illustrate the results of this experiment.

In FIG. 29C, most of the blood vessels completely disappear after the treatment. The same observation is seen 5 minutes after the treatment (images much longer after the treatment are not taken). There is also no sign of side effects such as purpura.

There are several possible theories that may contribute to this disappearance:

Thermal energy causes the blood vessels to constrict and force the blood out. The blood flow then becomes occluded.

Coagulated blood inside the vessels has a different spectral property and absorbs light less strongly. Therefore, they appear much fainter.

Skin tissue damage above the blood vessels causes a change in spectral property such that light cannot penetrate to the blood vessels underneath.

Damaged blood vessel walls have a different spectral property.

In order to verify the destruction of the blood vessels, punch biopsies are taken 1 hour after the treatment.

Figure 30:
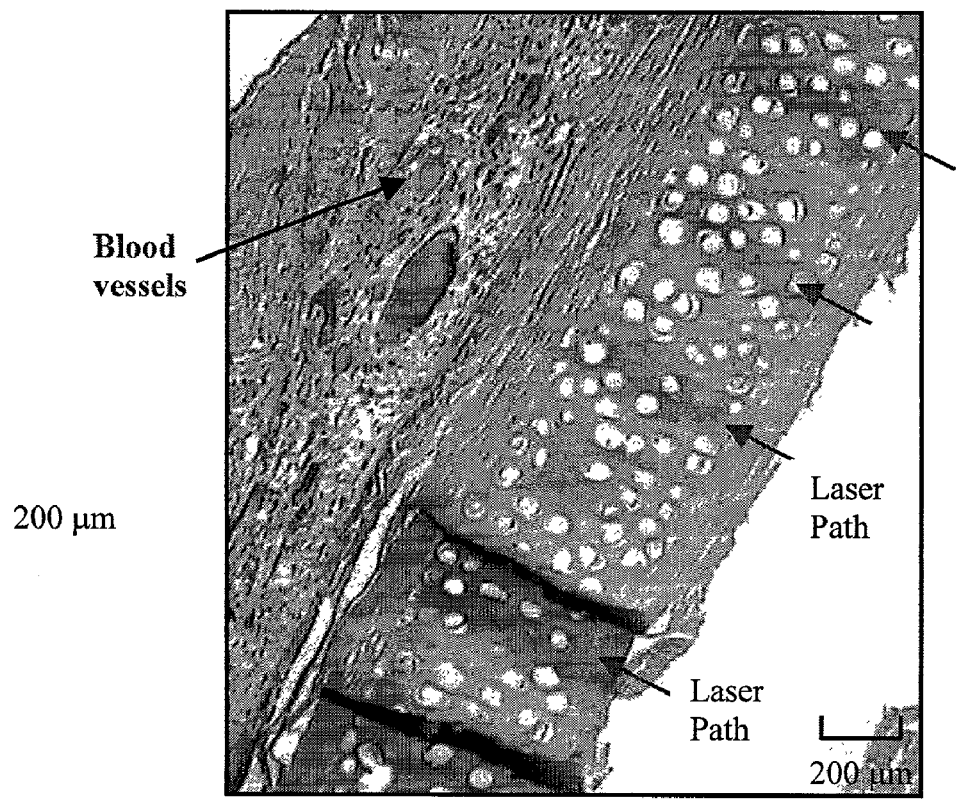
Figure 31:
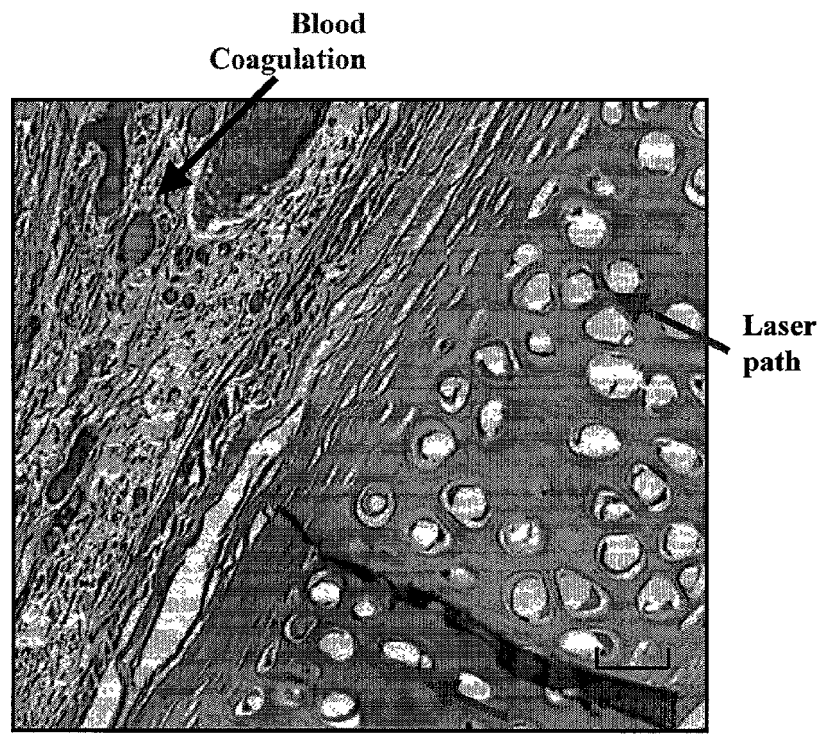

Histology samples from punch biopsies are prepared with the help of dermatologists at MGH. The histological results shown in FIG. 30 show agglutinated red blood cell and platelet thrombi confined to the blood vessels. The magnified image in FIG. 31 presents a close-up view of the blood coagulation and endothelial cell (around vessel wall) damage. These observations prove that the blood vessels have indeed by damaged by the laser energy.

The darker shades in the tissue region (red arrows) represent thermal damage. Notice that the tissue scarring is only confined to straight paths along which blood vessels reside. The rest of the tissues that are not in the path of the blood vessels are not damaged at all. If the same site is to be treated with a conventional laser device, this tissue damage will be seen throughout the entire region. Therefore, this serves to reiterate the fact that the Smart Scalpel is a safer treatment device. The Smart Scalpel has been tested successfully on a rabbit ear, whereby blood vessel damage is achieved without damage to the surrounding healthy tissue. The tissue imaging and laser treatment are still in their preliminary stages, and more extensive tests are required.

Physicians prefer the coagulation and collapse mechanism of vessel destruction to the hemorrhaging and reabsorption mechanism because the former treatment is less invasive. Also, if the laser causes a great amount of blood to spread throughout the tissue, the information from our imaging system will be imprecise. The computer may mistake this pooling of blood as blood vessels and begin to treat the wrong region of the skin.

The Smart Scalpel represents a new class of medical device which utilizes real-time information about tissue properties to selectively deliver laser energy to the specified blood vessel targets. The flexible system design allows precise and automatic control over the treatment parameters to achieve optimal treatment results.

The system bandwidth is 3.6 Hz with a Pentium II 500 MHz computer. This is achieved using the regional division strategy discussed in, and setting the number of targets N in each region to be 100 and the laser pulse width to be 1 ms. The bandwidth can be increased even more if faster instruments and computer are used. It is noted that computer 105 may be any computing or logic device adapted to perform the algorithms discussed above or any additional algorithms for any type of procedure designed for the Smart Scalpel system.

It is noted that the Smart Scalpel system may be used to design new treatments and algorithms. For example, the Smart Scalpel system may be used to collect different images of tissue having various characteristics. With a library of different images, it is possible to determine which the types of conditions (e.g., vascular lesions) a set of parameters for the Smart Scalpel is suitable to treat. In addition, this library can also be used to design separate algorithms, where each algorithm is tailored to treat a different type of condition (e.g., lesions) or to perform a different type of procedure. These algorithm "packages" are useful for using the Smart Scalpel as a platform technology (described above with reference to FIGS. 1A and 1B).

Optimization of PWS laser treatment on an individual patient basis may be improved with diagnostic methods that determine epidermal melanin concentration, distribution of vessel number and diameter as a function of depth, percentage oxygen saturation and blood flow velocity.

There are 3 non-invasive diagnostic sensing methods that measure important optical-thermal data to determine PWS anatomy and physiology, and which can be incorporated in the Smart Scalpel to provide complementary information. These are optical reflectance spectroscopy (ORS), infrared tomography (IRT), and optical low-coherence reflectometry (OLCR).

ORS is already used in the exemplary embodiment of the Smart Scalpel to identify blood vessels. However, ORS can also provide average optical PWS characteristics, such as dermal fractional blood volume, average superficial and deep vessel diameter and epidermal melanin absorption. The ORS inverse problem has not (yet) been solved and part of the effort is to infer what detailed anatomical data can be derived given the PWS reflectance spectrum.

IRT uses a fast infrared focal plane array camera to detect the increase in infrared emission at the tissue surface, which is induced by instantaneous heating of subsurface chromophores and subsequent thermal diffusion. IRT shows epidermal melanin absorption, diameter, location and temperature rise of the PWS vessels heated by incident laser light, therefore providing direct insight on treatment safety and depth achieved per pulse. This method requires use of advance numerical inversion algorithms.

Prior to the institution of therapy, IRT analysis of the PWS in response to a sub-therapeutic diagnostic laser pulse would provide information of the PWS characteristics. These information can then be used by the clinician to help select the optimal parameters (wavelength, pulse duration and radiation exposure) for the first treatment. At the next treatment, a second IRT record is made. Because many of the most superficial vessels were removed by the first treatment, IRT now images a deeper absorbing layer of PWS blood vessels. The optimal treatment parameters are then selected based on the IRT record.

OLCR is an advanced version of interferometric technique whereby the location and relative strength of optically scattering structures can be deduced. Results from OLCR are analogous to those from an ultrasound B-scan except that the imaging is performed optically and it has higher sensitivity and spatial resolution (1–10 μm).

OLCR may be used to determine the depth and diameter of PWS vessels in their three-dimensional dermal matrix, as well as percentage oxygen saturation and blood flow. OLCR, thus, allows evaluation of treatment depth following each pulse, and the biological response of the PWS microcirculation in response to laser irradiation.

Recursive Gaussian Filter (IIR)

The Recursive Gaussian Filtering discussed above will now be described in further detail. The IR is a recursive filtering structure that drastically reduces the computational effort required for smoothing and performing the first and second Gaussian derivatives. These operations are done with a fixed number of operations per output point independent of the resolution of the Gaussian function considered. The key to the approach is (1) the use of an exponentially based filter family and (2) the use of a recursive sequence.

This section will not explain the IIR concepts and the formula derivations, but rather give the results and methods of implementation. In addition, only the $4^{th}$ order Gaussian smoothing filter will be discussed.

The problem of recursive filter design deals with the determination of the coefficients $a_k$'s and $b_k$'s of a rational transfer function of the form:

$$H_a(z^{-1}) = \frac{\sum_{k=0}^{m-1} b_k z^{-(k-1)}}{1 + \sum_{k=1}^{n-1} a_k z^{-k}}, \quad (37)$$

which characterizes the following recursive system of order n $$y(i) = \sum_{k=0}^{m-1} b_k x(i-k) - \sum_{k=1}^{n} a_k y(i-k), \quad (38)$$

so that the rational transfer function $H_a(z^{-1})$ is exactly, or best approximates, the transfer function of the non-recursive system given by a FIR filter.

In the case where the order n is equal to 4, an operator $h_a(n)$ can be written in the general case as:

$$h_a(n) = \left[a_0\cos\left(\frac{w_0}{\sigma}n\right) + a_1\sin\left(\frac{w_0}{\sigma}n\right)\right] e^{\frac{b_0}{\sigma}n} + \left[c_0\cos\left(\frac{w_1}{\sigma}n\right) + c_1\sin\left(\frac{w_1}{\sigma}n\right)\right] e^{-\frac{b_1}{\sigma}n} \quad (39)$$

In the design of the IIR filter, the first step is to find out the set of coefficients a, b, c and w in order that the operator $h_a(n)$ approximates in the mean square error sense the Gaussian operator.

For the Gaussian smoothing function, the following coefficients are obtained with a normalized mean square error of $\epsilon^2 = 8.594099e{-}8$:

$$g_a(x) = \left[1.68\cos\left(0.6318\frac{x}{\sigma}\right) + 3.735\sin\left(0.6318\frac{x}{\sigma}\right)\right]e^{-1.783\frac{x}{\sigma}} - \quad (40)$$
$$\left[0.6803\cos\left(1.997\frac{x}{\sigma}\right) + 0.2598\sin\left(1.997\frac{x}{\sigma}\right)\right]e^{-1.723\frac{x}{\sigma}}.$$

To apply the design to a non-causal impulse response, h(n) can be transformed into a sum of causal sequences by splitting it into two halves $h_+(n)$ and $h_-(n)$. Then, $h(n) = h_+(n) + h_-(n)$, and with:

$$h_+(n) = \begin{cases} h(n) & n \geq 0 \\ 0 & n < 0 \end{cases}, \quad (41)$$

$$h_-(n) = \begin{cases} 0 & n \geq 0 \\ h(n) & n < 0 \end{cases}. \quad (42)$$

$h_+(n)$ and $h_-(n)$ are causal with opposite direction and we can compute a recursive system $H_+(z^{-1})$ and $H_-(z)$ having impulse responses close to $h_+(n)$ and $h_-(n)$ respectively.

$$H_+(z^{-1}) = \frac{n_{00}^+ + n_{11}^+ z^{-1} + n_{22}^+ z^{-2} + n_{33}^+ z^{-3}}{1 + d_{11}^+ z^{-1} + d_{22}^+ z^{-2} + d_{33}^+ z^{-3} + d_{44}^+ z^{-4}}, \quad (43)$$

$$H_-(z) = \frac{n_{11}^- z^1 + n_{22}^- z^2 + n_{33}^- z^3 + n_{44}^- z^4}{1 + d_{11}^- z^1 + d_{22}^- z^2 + d_{33}^- z^3 + d_{44}^- z^4}. \quad (44)$$

The two z-transforms in Equations (43) and (44) correspond to two transfer functions of stable $4^{th}$ order filters recursing from the left to the right for the causal sequence (41), and from the right to the left for the anticausal sequence (42). They are implemented by applying the recursive sequence $$y_k^+ = n_{00}^+ x_k + n_{11}^+ x_{k-1} + n_{22}^+ x_{k-2} + n_{33}^+ x_{k-3} - d_{11}^+ y_{k-1}^+ - d_{22}^+ y_{k-2}^+ - d_{33}^+ y_{k-3}^+ - d_{44}^+ y_{k-4}^+,$$

$$y_k^- = n_{11}^- x_{k+1} + n_{22}^- x_{k+2} + n_{33}^- x_{k+3} + n_{44}^- x_{k+4} - d_{11}^- y_{k+1}^- - d_{22}^- y_{k+2}^- - d_{33}^- y_{k+3}^- - d_{44}^- y_{k+4}^-,$$

$$y_k = y_k^+ + y_k^- \quad (k=1, \ldots, N). \quad (45)$$

where $x_k$ is the input to the filter and $y_k$ is the output.

The coefficients $n_{ij}$ and $d_{ij}$ can be computed by applying the following equations derived from the z transform of (38):

$$n_{33}^+ = e^{-\frac{b_1}{\sigma} - 2\frac{b_0}{\sigma}}\left[c_1\sin\left(\frac{w_1}{\sigma}\right) - c_0\cos\left(\frac{w_1}{\sigma}\right)\right] +$$
$$e^{-\frac{b_0}{\sigma} - 2\frac{b_1}{\sigma}}\left[a_1\sin\left(\frac{w_0}{\sigma}\right) - a_0\cos\left(\frac{w_0}{\sigma}\right)\right],$$

$$n_{22}^+ = 2e^{-\frac{b_0}{\sigma} - \frac{b_1}{\sigma}}\left[(a_0 + c_0)\cos\left(\frac{w_1}{\sigma}\right)\cos\left(\frac{w_0}{\sigma}\right) - a_1\cos\left(\frac{w_1}{\sigma}\right)\sin\left(\frac{w_0}{\sigma}\right) - c_1\cos\left(\frac{w_0}{\sigma}\right)\sin\left(\frac{w_1}{\sigma}\right)\right] + c_0 e^{-2\frac{b_0}{\sigma}} + a_0 e^{-2\frac{b_1}{\sigma}},$$

$$n_{11}^+ = e^{-\frac{b_1}{\sigma}}\left[c_1\sin\left(\frac{w_1}{\sigma}\right) - (c_0 + 2a_0)\cos\left(\frac{w_1}{\sigma}\right)\right] +$$
$$e^{-\frac{b_0}{\sigma}}\left[a_1\sin\left(\frac{w_0}{\sigma}\right) - (2c_0 + a_0)\cos\left(\frac{w_0}{\sigma}\right)\right],$$

$$n_{00}^+ = a_0 + c_0,$$

$$d_{44}^+ = e^{-2\frac{b_0}{\sigma} - 2\frac{b_1}{\sigma}},$$

$$d_{33}^+ = -2\cos\left(\frac{w_0}{\sigma}\right)e^{-\frac{b_0}{\sigma} - 2\frac{b_1}{\sigma}} - 2\cos\left(\frac{w_1}{\sigma}\right)e^{-\frac{b_1}{\sigma} - 2\frac{b_0}{\sigma}},$$

$$d_{22}^+ = 4\cos\left(\frac{w_1}{\sigma}\right)\cos\left(\frac{w_0}{\sigma}\right)e^{-\frac{b_0}{\sigma} - \frac{b_1}{\sigma}} + e^{-2\frac{b_1}{\sigma}} + e^{-2\frac{b_0}{\sigma}},$$

$$d_{11}^+ = -2e^{-\frac{b_1}{\sigma}}\cos\left(\frac{w_1}{\sigma}\right) - 2e^{-\frac{b_0}{\sigma}}\cos\left(\frac{w_0}{\sigma}\right),$$

$d_{ii}^- = d_{ii}^+$ $i=1, \ldots, 4$, $n_{ii}^- = n_{ii}^+ - d_{ii}^+ n_{00}^+$ $i=1, \ldots, 3$, $n_{ii}^- = -d_{ii}^+ n_{00}^+$ $i=4$.

Before implementing the recursive sequence, the IIR filter may be normalized. To do this, each coefficient in the operator $h_a(n)$ may be scaled by a factor which satisfies a given constraint. In the case of the smoothing operator used to approximate the Gaussian filter, the following constraint is required:

$$N_g\left(\sum_{n=-\infty}^{\infty} h_a(n)\right) = 1, \text{ where } N_g \text{ is the scale factor.} \quad (46)$$

This scale factor can be numerically computed and divided to each coefficient before applying the recursive sequence.

In the case of a $4^{th}$ order IIR filter, the number of operations per pixel is 31. This is equivalent to implementing a FIR filter with 16 coefficients. In general, the width of the FIR filter used is greater than 25 (equivalent to 49 operations per pixel), and therefore, this justifies the use of the IIR filter. In addition, the speed of IIR convolution is unaffected by the choice of $\sigma$, while that of the FIR filter increases with $\sigma$ because the filter becomes wider.

The number of operations reduces to 23 per pixel in the case of $3^{rd}$ order IIR filters, and 15 per pixel in the case of $2^{nd}$ order filters. These are achieved, of course, at the expense of accuracy. It is found that $3^{rd}$ order filters provides a good tradeoff.

Mathematic Theories for Line Detector

Given an image function F(x,y), the above theories for the line detection described will now be described in further detail its quadratic polynomial approximation is given by:

$$F(x,y) = R + (R_x x + R_y y) + \tfrac{1}{2}(R_{xx} x^2 + 2R_{xy} xy + R_{yy} y^2), \quad (47)$$

where $R_x$, $R_y$, $R_{xx}$, $R_{xy}$, and $R_{yy}$ are the locally estimated derivatives at (x,y) that are obtained by convolving the image with the appropriate Gaussian kernels.

To extract the lines in an image, the solution of zero crossing may be determined. This is equivalent to finding the solution to the polynomial (47) where the first derivative along the unit vector $\vec{n}$ goes to zero. $\vec{n}$ is chosen such that it is pointing in the direction perpendicular to the line. This solution is also the mathematical proof of Equation (26).

From Equation (47), $$F(x, y) = R + (R_x x + R_y y) + \frac{1}{2}(R_{xx}x^2 + 2R_{xy}xy + R_{yy}y^2),$$

$$\frac{\partial}{\partial x}F(x, y) = R_x + R_{xx}x + R_{xy}y, \quad (48)$$

$$\frac{\partial}{\partial y}F(x, y) = R_y + R_{yy}y + R_{xy}x. \quad (49)$$

From Equation (21),

First Derivative along $\vec{n} = 0$ $$\hat{n}_x \frac{\partial}{\partial x}F(x, y) + \hat{n}_y \frac{\partial}{\partial y}F(x, y) = 0$$

Substituting from Equations (48) and (49), $$(R_x\hat{n}_x + R_y\hat{n}_y) + (R_{xx}\hat{n}_x + R_{xy}\hat{n}_y)x + (R_{yy}\hat{n}_y + R_{xy}\hat{n}_x)y = 0. \quad (50)$$

Since the solution (x,y) may lie along $\vec{n}$, therefore:

$$(x, y) = (t\hat{n}_x, t\hat{n}_y), \text{ where t is a constant.} \quad (51)$$

Substituting Equation (51) into (50), $$(R_x\hat{n}_x + R_y\hat{n}_y) + (R_{xx}\hat{n}_x + R_{xy}\hat{n}_y)t\hat{n}_x + (R_{yy}\hat{n}_y + R_{xy}\hat{n}_x)t\hat{n}_y = 0$$

$$\Rightarrow t = -\frac{R_x\hat{n}_x + R_y\hat{n}_y}{R_{xx}\hat{n}_x^2 + 2R_{xy}\hat{n}_x\hat{n}_y + R_{yy}\hat{n}_y^2}$$

Therefore, from (51), the position where the first derivative=0 is:

$$x = \left(-\frac{R_x\hat{n}_x + R_y\hat{n}_y}{R_{xx}\hat{n}_x^2 + 2R_{xy}\hat{n}_x\hat{n}_y + R_{yy}\hat{n}_y^2}\right)\hat{n}_x,$$

$$y = \left(-\frac{R_x\hat{n}_x + R_y\hat{n}_y}{R_{xx}\hat{n}_x^2 + 2R_{xy}\hat{n}_x\hat{n}_y + R_{yy}\hat{n}_y^2}\right)\hat{n}_y.$$

(Proof for Equation (26))

The eigenvectors and eigenvalues of the Hessian matrix can be found in a numerically stable and efficient way by using one Jacobi rotation.

Given a 2×2, real symmetric matrix $$A = \begin{bmatrix} a & b \\ b & d \end{bmatrix},$$

the step to find the eigenvectors and eigenvalues are:

$$\tilde{t} = \frac{2b}{a - d}, \quad t = \frac{\tilde{t}}{1 + \sqrt{1 + \tilde{t}^2}}, \quad c = \frac{1}{\sqrt{1 + t^2}}, \quad s = ct.$$

Then the eigenvalues and eigenvectors are given by:

$$\lambda_1 = (a + tb) \quad \vec{e}_1 = \begin{bmatrix} c \\ s \end{bmatrix} \quad (52)$$

$$\lambda_2 = (d - tb) \quad \vec{e}_2 = \begin{bmatrix} -s \\ c \end{bmatrix}, \quad (53)$$

where $\|\vec{e}_1\|$ and $\|\vec{e}_2\|$ are equal to 1.

The foregoing description regarding the treatment of PWS is merely an exemplary embodiment of the present invention and does not in any way limit the scope thereof.

For example, besides programming computer 105 to "switch on" treatment laser 115 when it sees a target, it can also be programmed to do the opposite. For example, laser 115 may be applied continuously until computer 105 notices that the treatment is complete and instructs laser 115 to stop. This application can be used, for instance, when trying to remove just enough surface tissue from a region without injuring the tissues underneath. As soon as the imaging system detects the tissue underneath, it may stop the laser and move to the next target.

As described before, Smart Scalpel system 100 is different because it is programmed with "behavioral" conditions, and it may treat different people very differently. For example, if a person has a few large vessels, the treatment process may be fast, and the laser energy used may be large; on the other hand, if he has many small vessels, the treatment process may be longer, and the energy may be smaller.

The many desirable attributes of Smart Scalpel system 100 have the potential not only to improve performance in current microsurgical procedures, but also to facilitate the development of new treatments not yet feasible with existing technology. The accuracy and reliability of present-day procedures may be enhanced and collateral damage minimized through quantitative, on-line assessment of procedure efficacy. This system of real-time feedback has great potential to increase patient comfort, shorten recovery times, and decrease the overall cost per procedure.

As noted before, probe 140 may be a handheld instrument or an automated apparatus. An automated delivery system can produce more efficient and better controlled treatments than free hand methods. It also allows longer endurance than humans in the same task. Many experts have demonstrated that the precise control of dosimetry is an important criterion for successful laser therapy. Thus, automated treatment devices may improve the treatment results by using lasers in an optimal fashion.

Two categories of automated treatment devices are: scanners and automated handpieces. In the first category, scanners include the Multiscan and the Scanall. These instruments automatically scan the laser spot over a tissue volume using mirrors. Multiscan may produce a 5 mm spot diameter, and the Scanall system may use a 0.5 mm spot diameter. The velocity of scanning (50 to 300 mm/s) is adjusted to provide the appropriate incident fluence. Both scanners work without contacting the skin, and Scanall uses a video camera to obtain an image of the tissue volume, and this image is mapped to the computer to limit the laser treatment to a selected target.

Hexascan and CC-scan are automated handpieces controlled by a scanner mechanism composed of two stepper motors. The motors are controlled by a microprocessor so they can be programmed to scan the laser across the treatment area in a variety of predefined patterns. These patterns are arranged so that no laser spot is placed adjacent to another spot, thus limiting thermal injury. The Hexascan handpiece contains a power meter and a shutter to ensure that there is ample cooling between two adjacent spots. Comparing the results between the "free hand point-by-point" technique and the Hexascan automated handpiece reveals a factor of two increase in the percentage of good clinical results. Treatment duration may be reduced to 20% of the point-by-point technique, and a drastic reduction in hypertrophic scarring may be observed.

As noted before, Smart Scalpel 100 may be used to perform many different procedures. A number of additional examples will now be described.

Hair Removal

FIGS. 32A, 32B, 32C, and 32D illustrate imaging a hair follicle for hair removal using Smart Scalpel system 100 according to an embodiment of the invention.

As shown in FIG. 32A, a hair follicle 3205 may lie several mm's beneath skin 3210 and hair shaft 3215 may emerge from skin 3210 at an angle. Each hair in an area may be at a different angle.

FIG. 32B illustrates a surface image of hair imaged at, say 800 nm. As shown in FIG. 32B, the end of hair 3220, which goes into the skin, may be identified because its contrast gradually disappears into the skin. Based on contrast so detected and calculated direction (FIG. 32C) and distance (FIG. 32D), the location of hair follicles may be inferred.

Figure 33:
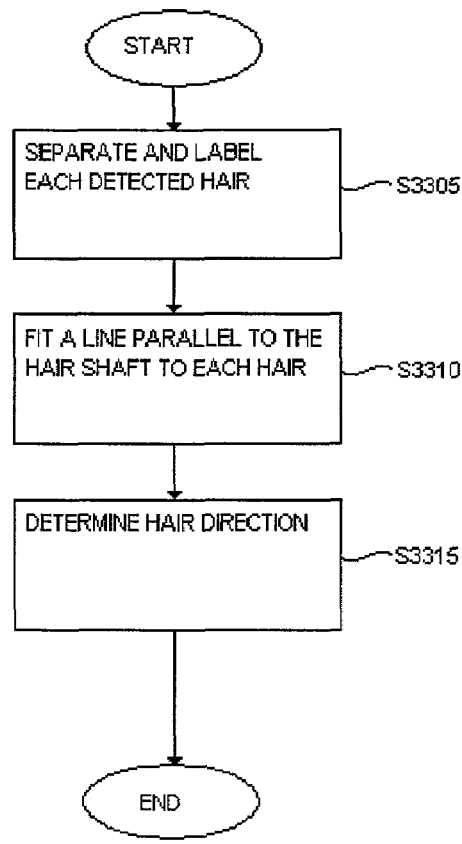
FIG. 33 is a diagram showing a process of imaging in accordance with an embodiment of the present invention.

Therefore, computer 105 can automatically identify a "line" of possible follicle positions, as illustrated above, based upon a programmed algorithm. As an example, such an algorithm may include the following steps, as illustrated in FIG. 33.

At step S3300, computer 105 may perform an image segmentation to distinguish hair from skin based upon, say, contrast, shape or hair color. At step S3305, each hair may be labeled to separate them out so that each hair may be processed individually. Next, for each hair, a line parallel to the hair shaft and passing through the midpoint of the hair may be fitted, as shown by step S3310. This line can be fitted either (1) using least square line fitting, (2) finding the axis of least inertia, (3) performing a Hough transform to detect the line, (4) edge detection, (5) skeletonization, or (6) a combination of these techniques.

After fitting the line, it is determined which end goes into the skin, as illustrated by step S3315. This determination may be made by observing the gradient of the brightness change along the fitted line. The end going into the skin would have smooth gradients, while the other end would have a very sharp gradient. As a result, the possible location of the hair follicle along this line at a particular distance away from the hair may be identified, treatment (hair removal) laser may be directed at this inferred location.

If the hair is almost the same color as the skin, Smart Scalpel system 100 may deliberately dye the hair or the skin so that they can be distinguished easily.

Cancer Treatment/Age spot/Acne/Scars

For cancer treatment, some cancers change color or fluoresce when particular dyes or chemicals are applied. Therefore, Smart Scalpel system 100 may include algorithms that specifically target tissues that have the particular colors that these cancers change to after such dyes or chemicals are applied.

Age spots, acne or scars also have colors different from the rest of the skin, and can be distinguished using a color distinction algorithm.

Image segmentation based on color is very useful. A condition to be targeted may not be obvious to Smart Scalpel system 100, but certain processes may be used to "dye" the targets as distinguished from non-target tissue. Likewise, non-target tissue may be "dyed" and Smart Scalpel system 100 may target only "non-colored" regions.

An example of the use of "dyes" may be the treatment of wrinkles.

Wrinkles

Wrinkles may be drawn over with a pen Smart Scalpel system 100 may be programmed to target the pen marks.

Besides pen color, wrinkles may be identified based on shadow(s) or contrast created by folds of the wrinkles. A line detection algorithm may be used to detect them.

It is further noted that the rapid feedback, real-time diagnosis Smart Scalpel system may be programmed with secondary characteristics for identifying treatment targets. For example, straight, curved, large, and small vessels may be located and identified by the Smart Scalpel for a number of different treatments.

As mentioned before, based on the platform technology of the present invention, the Smart Scalpel has a wide variety of uses, such as brain scanning and surgery, veterinary surgery, etc. It may further be implemented as a non-invasive tool in the midst of an invasive procedure. For instance, the imaging and processing systems for target identification may be implemented in an endoscope for exploratory procedures. Thus, given the flexibility of the system and the variety of use, the Smart Scalpel system of the present invention is not limited to the imaging and targeting schemes of the embodiments described above. For example, the imaging light may include one or more selected wavelengths (e.g., a selected spectrum of light, say, white light), and the treatment energy source may include one or more selected energy levels, wavelengths, etc.

It will thus be seen that the objects set forth above, among those made apparent from the preceding description, are efficiently attained and, because certain changes may be made in carrying out the above method(s) and in the construction(s) set forth without departing from the spirit and scope of the invention, it is intended that all matter contained in the above description and shown in the accompanying drawings shall be interpreted as illustrative and not in a limiting sense.

It is to be understood that the following claims are intended to cover all of the generic and specific features of the invention herein described and all statements of the scope of the invention which, as a matter of language, might be said to fall therein.

What is claimed is:

1. A method of using a feedback control to non-invasively identify and locate one or more subsurface targets based on predetermined conditions for selective laser treatment at a tissue surface area, comprising the steps of:
   a) identifying the location of the one or more subsurface targets in the tissue surface area by:
      i) directing one of a polarized and an unpolarized light having a predetermined wavelength at the tissue surface area;
      ii) detecting one or more reflections of said light using a multi-dimensional photo-sensor;
      iii) measuring one or more characteristics indicative of the physio-chemical properties for each of the one or more subsurface targets by automatically analyzing the reflections detected by said photo-sensor and comparing the analyzed reflections with the predetermined conditions, said predetermined conditions defined at least in part by one of predetermined image analysis and one or more mathematical treatment algorithms relating to features of an image; and b) treating the one or more subsurface targets identified during the identification step by automatically applying a laser of a predetermined wavelength and a predetermined power to the one or more subsurface targets in accordance with the one or more characteristics; and c) automatically adjusting one or more parameters of the laser in real time in accordance with the one or more characteristics until treatment is complete.

2. The method of claim 1, wherein the one or more characteristics include at least one of a size, a shape, a color, a contrast, a brightness, a pattern, a structure, and a treatment status of tissue at the one or more subsurface targets.

3. The method of claim 1, wherein the one or more characteristics include at least one of photometric, spectrometric, and topological properties of tissue at the one or more subsurface targets.

4. The method of claim 1, further comprising the step of pulsing the laser on and off to control laser delivery to the one or more subsurface targets.

5. The method of claim 1, wherein the one or more parameters include at least one of a spot size, a pulse width, a wavelength and a power of the laser.

6. The method of claim 5, wherein the spot size is adjusted through actuated movement of one or more optical components.

7. The method of claim 6, wherein the one or more optical components includes one or more focusing lenses.

8. The method of claim 1, wherein the identification step provides rapid feedback for tracking rapid relative movement between the laser and the one or more subsurface targets so that laser-targeting error is minimized.

9. The method of claim 8, wherein the rapid feedback has a bandwidth of more than 0.5 Hz.

10. The method of claim 8, further comprising the step of performing real time diagnosis of treatment results and efficacy of the treatment by repeating the identification step after the treating step.

11. The method of claim 1, wherein the feedback control is one of semi-automatic and fully automatic.

12. The method of claim 1, wherein a spot size of the laser is less than 3 mm.

13. The method of claim 1, wherein the laser is a continuous wave laser.

14. The method of claim 1, wherein the target location determined at the identification step for said each subsurface target is determined by inference from a corresponding location.

15. The method of claim 14, wherein said inference is based on the predetermined conditions.

16. The method of claim 1, wherein said feedback control is one of a closed-loop feedback control and a quasi-closed-loop feedback control.

17. The method of claim 1, further comprising the step of determining a polarization of the one or more reflections, wherein the location and one or more characteristics for each of the one or more subsurface targets are determined based upon the polarization of the one or more reflections.

18. The method of claim 1, wherein said treating step includes one of heating and modifying the one or more subsurface targets.

19. An apparatus adapted and configured to use feedback control to non-invasively identify and locate one or more subsurface targets based on predetermined conditions for selective laser treatment at a tissue surface area, comprising:

a) means for identifying the location of the one or more subsurface targets in the tissue surface area including:
   i) means for directing one of a polarized and an unpolarized light having a predetermined wavelength at the tissue surface area;
   ii) means for detecting one or more reflections of said light including a multi-dimensional photo-sensor; and
   iii) means for measuring one or more characteristics indicative of the physio-chemical properties for each of the one or more subsurface targets, wherein the measuring means is adapted and configured to automatically analyze the reflections detected by said photo-sensor and compare the analyzed reflections with the predetermined conditions, said predetermined conditions defined at least in part by one of predetermined image analysis and one or more mathematical treatment algorithms relating to features of an image;

b) means for treating the one or more subsurface targets identified by the identifying means including a laser, wherein the treating means is adapted and configured to automatically apply the laser at a predetermined wavelength and a predetermined power to the one or more subsurface targets in accordance with the one or more characteristics; and c) means for automatically adjusting one or more parameters of the laser in real time in accordance with the one or more characteristics until treatment is complete.

20. The apparatus of claim 19, wherein the one or more characteristics include at least one of a size, a shape, a color, a contrast, a brightness, a pattern, a structure, and a treatment status of tissue at the one or more subsurface targets.

21. The apparatus of claim 19, wherein the one or more characteristics include at least one of photometric, spectrometric, and topological properties of tissue at the one or more subsurface targets.

22. The apparatus of claim 19, wherein the treating means pulses the laser on and off to control laser delivery to the one or more subsurface targets.

23. The apparatus of claim 19, wherein the one or more parameters include at least one of a spot size, a pulse width, a wavelength and a power of the laser.

24. The apparatus of claim 23, wherein the spot size is adjusted through actuated movement of one or more optical components.

25. The apparatus of claim 24, wherein the one or more optical components includes one or more focusing lenses.

26. The apparatus of claim 19, wherein the directing, detecting, and measuring means perform rapid feedback for tracking rapid relative movement between the laser and the one or more subsurface targets so that laser-targeting error is minimized.

27. The apparatus of claim 26, wherein the rapid feedback has a bandwidth of more than 0.5 Hz.

28. The apparatus of claim 26, wherein the directing, detecting, and measuring means perform real time diagnosis of treatment results and efficacy of the laser.

29. The apparatus of claim 19, wherein the feedback control is one of semi-automatic and fully automatic.

30. The apparatus of claim 19, wherein a spot size of the laser is less than 3 mm.

31. The apparatus of claim 19, wherein the laser is a continuous wave laser.

32. The apparatus of claim 19, wherein the measuring means determines the location for said each subsurface target by inference from a corresponding location detected by said detecting means.

33. The apparatus of claim 32, wherein said inference is based on the predetermined conditions.

34. The apparatus of claim 19, wherein said feedback control is one of a closed-loop and a quasi-closed-loop feedback control.

35. The apparatus of claim 19, further comprising means for determining a polarization of the one or more reflections, wherein the location and one or more characteristics for each of the one or more subsurface targets are determined based upon the determined polarization.

36. The apparatus of claim 19, wherein treatment performed by the treating means includes one of heating and modifying for respectively heating and modifying the one or more subsurface targets.

37. An apparatus adapted and configured to use feedback control to non-invasively identify and locate one or more subsurface targets based on predetermined conditions for selective laser treatment at a tissue surface area, comprising:
  a) a detector for identifying the location of the one or more subsurface targets in the tissue surface area, the detector including:
    i) an optical pathway operably coupled to a light source adapted and configured to direct one of a polarized and an unpolarized light having a predetermined wavelength at the tissue surface area;
    ii) a multi-dimensional photo-sensor adapted and configured to detect one or more reflections of said light; and
    iii) a processor for evaluating one or more characteristics indicative of the physio-chemical properties for each of the one or more subsurface targets, by automatically analyzing the reflections detected by the photo-sensor wherein the processor is adapted and configured to compare the analyzed reflections with the predetermined conditions, the predetermined conditions defined at least in part by one of predetermined image analysis and one or more mathematical treatment algorithms relating to features of an image;
  b) a laser for treating the one or more subsurface targets identified by the detector, wherein the laser is adapted and configured to automatically apply light at a predetermined wavelength and a predetermined power to the one or more subsurface targets in accordance with the one or more characteristics; and
  c) wherein the processor is adapted and configured to automatically adjust one or more parameters of the laser in real time in accordance with the one or more characteristics by moving at least one optical components in a path defined by the laser until treatment is complete.

* * * * *

UNITED STATES PATENT AND TRADEMARK OFFICE
CERTIFICATE OF CORRECTION

PATENT NO. : 7,217,266 B2  Page 1 of 1
APPLICATION NO. : 09/870544
DATED : May 15, 2007
INVENTOR(S) : Richard R. Anderson et al.

It is certified that error appears in the above-identified patent and that said Letters Patent is hereby corrected as shown below:

At col. 1, line 4, please insert the following text:

-- STATEMENT AS TO RIGHTS TO INVENTIONS MADE UNDER FEDERAL SPONSORED RESEARCH AND DEVELOPMENT

This invention was made with government support under Grant No. DAMD17-99-2-9001 awarded by the U.S. Department of the Army. The U.S. Government has certain rights in this invention. --

Signed and Sealed this

Seventh Day of July, 2009

JOHN DOLL
*Acting Director of the United States Patent and Trademark Office*